United States Patent
Tsai et al.

(10) Patent No.: US 11,141,262 B2
(45) Date of Patent: Oct. 12, 2021

(54) BONE IMPLANT

(71) Applicant: INDUSTRIAL TECHNOLOGY RESEARCH INSTITUTE, Hsinchu (TW)

(72) Inventors: Pei-I Tsai, Hsinchu (TW); Hsin-Hsin Shen, Taipei (TW); Kuo-Yi Yang, Hsinchu (TW); Chih-Chieh Huang, Miaoli County (TW); Shih-Ping Lin, Kaohsiung (TW); De-Yau Lin, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 144 days.

(21) Appl. No.: 16/230,666

(22) Filed: Dec. 21, 2018

(65) Prior Publication Data

US 2020/0197155 A1 Jun. 25, 2020

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0441* (2013.01); *A61B 2017/0445* (2013.01); *A61B 2017/0458* (2013.01); *A61F 2002/0817* (2013.01); *A61F 2002/0858* (2013.01)

(58) Field of Classification Search
CPC .............. A61F 2/0811; A61B 17/0401; A61B 17/0441; A61B 17/0445; A61B 17/0458
See application file for complete search history.

(56) References Cited

U.S. PATENT DOCUMENTS

| 6,503,251 | B1 | 1/2003 | Shadduck | |
|---|---|---|---|---|
| 6,855,168 | B2 * | 2/2005 | Crozet | A61F 2/442 623/17.11 |
| 8,894,661 | B2 * | 11/2014 | McDevitt | A61B 17/809 606/104 |
| 9,155,531 | B2 * | 10/2015 | Housman | A61B 17/8877 |
| 9,579,188 | B2 * | 2/2017 | Bowman | A61F 2/0805 |
| 10,022,118 | B2 | 7/2018 | Norton et al. | |
| 2006/0276895 | A1 | 12/2006 | Pellegrino et al. | |
| 2008/0154314 | A1 * | 6/2008 | McDevitt | A61B 17/8095 606/304 |
| 2009/0319043 | A1 | 12/2009 | McDevitt et al. | |

(Continued)

FOREIGN PATENT DOCUMENTS

| CN | 102137639 A | 7/2011 |
|---|---|---|
| CN | 102325505 A | 1/2012 |

(Continued)

OTHER PUBLICATIONS

TW Office Action in application No. 107146513 dated Aug. 2, 2019.

(Continued)

*Primary Examiner* — Brian A Dukert

(74) *Attorney, Agent, or Firm* — Maschoff Brennan

(57) ABSTRACT

A bone implant includes at least one spiral and at least one pillar. The spiral surrounds an accommodating space. The pillar is disposed in the accommodating space and connected to the spiral. The pillar has at least one notch.

16 Claims, 25 Drawing Sheets

(56) References Cited

U.S. PATENT DOCUMENTS

| | | | |
|---|---|---|---|
| 2015/0250513 A1* | 9/2015 | De Lavigne Sainte Suzanne ....... | A61B 17/866 606/304 |
| 2016/0100870 A1* | 4/2016 | Lavigne ............ | A61B 17/7064 606/304 |
| 2016/0166301 A1 | 6/2016 | Papangelou et al. | |
| 2017/0156879 A1* | 6/2017 | Janowski ................ | A61F 2/447 |
| 2017/0189009 A1 | 7/2017 | Dougherty et al. | |

FOREIGN PATENT DOCUMENTS

| | | |
|---|---|---|
| CN | 102781370 A | 11/2012 |
| CN | 105163672 A | 12/2015 |
| CN | 105877798 A | 8/2016 |
| CN | 205458853 U | 8/2016 |
| CN | 106687056 A | 5/2017 |
| TW | 201513826 A | 4/2015 |
| TW | M554773 U | 2/2018 |
| WO | 2005122969 A1 | 12/2005 |

OTHER PUBLICATIONS

European Search Report in application No. 18 21 5690 dated Jul. 3, 2019.

Altinel, et al., Suture anchor fixation strength with or without augmentation in osteopenic and severely osteoporotic bones in rotator cuff repair: A biomechanical study on polyurethane foam model, Journal of Orthopaedic Surgery and Research, Aug. 2014, 8 pages.

Bedi, et al., Differences in Tendon Graft Healing Between the Intra-articular and Extra-articular Ends of a Bone Tunnel, HSSJ, Dec. 4, 2008, 7 pages.

Carbonel, et al., Single-row versus double-row arthroscopic repair in the treatment of rotator cuff tears: a prospective randomized clinical study, International Orthopaedics (SICOT), May 16, 2012, pp. 1877-1883.

Chaudhry, et al., A review of suture anchors, Orthopaedics and Trauama, Dec. 2016, 8 pages.

Dhawan, et al., Complications of Bioabsorbable Suture Anchors in the Shoulder, AJSM, Aug. 19, 2011, 7 pages.

Khoury, et al., A Novel Method to Determine Suture Anchor Loading After Rotator Cuff Repair A Study of Two Double-Row Techniques, Bulletin of the NYU Hospital for Joint Diseases 2010; 68(1); pp. 25-28.

Kim et al., Comparison of Bioabsorbable Suture Anchor Fixation on the Tibial Side for Anterior Cruciate Ligament Reconstruction Using Free Soft Tissue Graft-Experimental Laboratory Study on Porcine Bone-, Yonsei Med, vol. 55, No. 3, May 2014, 6 pages.

Liu et al., A biomechanical study of different techniques in medial patellofemoral ligament reconstruction, Int J Clin Exp Med, Aug. 30, 2016, pp. 15235-15242.

Nagra, et al., Mechanical properties of all-suture anchors for rotator cuff repair, Bone Joint Research, vol. 6, No. 2, Feb. 2017, pp. 82-89.

Pietschmann, et al., Pullout strength of suture anchors in comparison with transosseous sutures for rotator cuff repair, Knee Surg. Sports Traumatol Arthrosc., Jan. 9, 2008, pp. 504-510.

Schneeberger, et al., Mechanical Strength of Arthroscopic Rotator Cuff Repair Techniques, The Journal of Bona and Joint Surgery, vol. 84-A, No. 12, Dec. 2002, pp. 2152-2160.

Strauss, et al., The Effect of the Angle of Suture Anchor Insertion on Fixation Failure at the Tendon-Suture Interface After Rotator Cuff Repair: Deadman's Angle Revisited, The Journal of Arthroscopic and Related Surgery, vol. 25, No. 6, Jun. 2009, pp. 597-602.

CN Office Action in Application No. 201811615550.9 dated Oct. 28, 2020.

* cited by examiner

BONE IMPLANT

TECHNICAL FIELD

The disclosure relates to a bone implant, more particularly a flexible bone implant.

BACKGROUND

When human bones, tendons, ligaments or other human tissues are damaged to a certain extent, doctors may decide to operate a surgery for repair the damaged part, such as to relocate the fractured fragments onto their original positions and then to fix them in position with sutures and a bone implant (e.g., a bone screw) for them to self-repair, or to put an artificial implant in human body to replace the damaged part.

Fracture is common occurs in the shoulder, knee or other movable human portions, but the artificial implant is rigid and therefore to limit the movement of the portion it is implanted, which may make it difficult to move their fractured portion freely or may break the artificial implant as the movement exceeds the limitation.

SUMMARY

Accordingly, the disclosure provides a bone implant which is more flexible and thus capable of decreasing the movement limitation to the injury portion and preventing the bone implant from being accidently detached.

One embodiment of the disclosure provides a bone implant. The bone implant includes at least one helix body and at least one pillar. The helix body surrounds an accommodating space. The pillar is disposed in the accommodating space and connected to the helix body. The pillar has at least one notch.

According to the bone implant as discussed above, the bone implant has the pillar to maintain the overall structural strength and has the notches to improve the flexibility. As such, the bone implants of the disclosure are able to decrease the movement limitation to the injury portion and prevent themselves from being detached.

The aforementioned summary and the following detailed description are set forth in order to provide a thorough understanding of the disclosed embodiment and provide a further explanations of claims of the disclosure.

DETAILED DESCRIPTION

Figure 1:
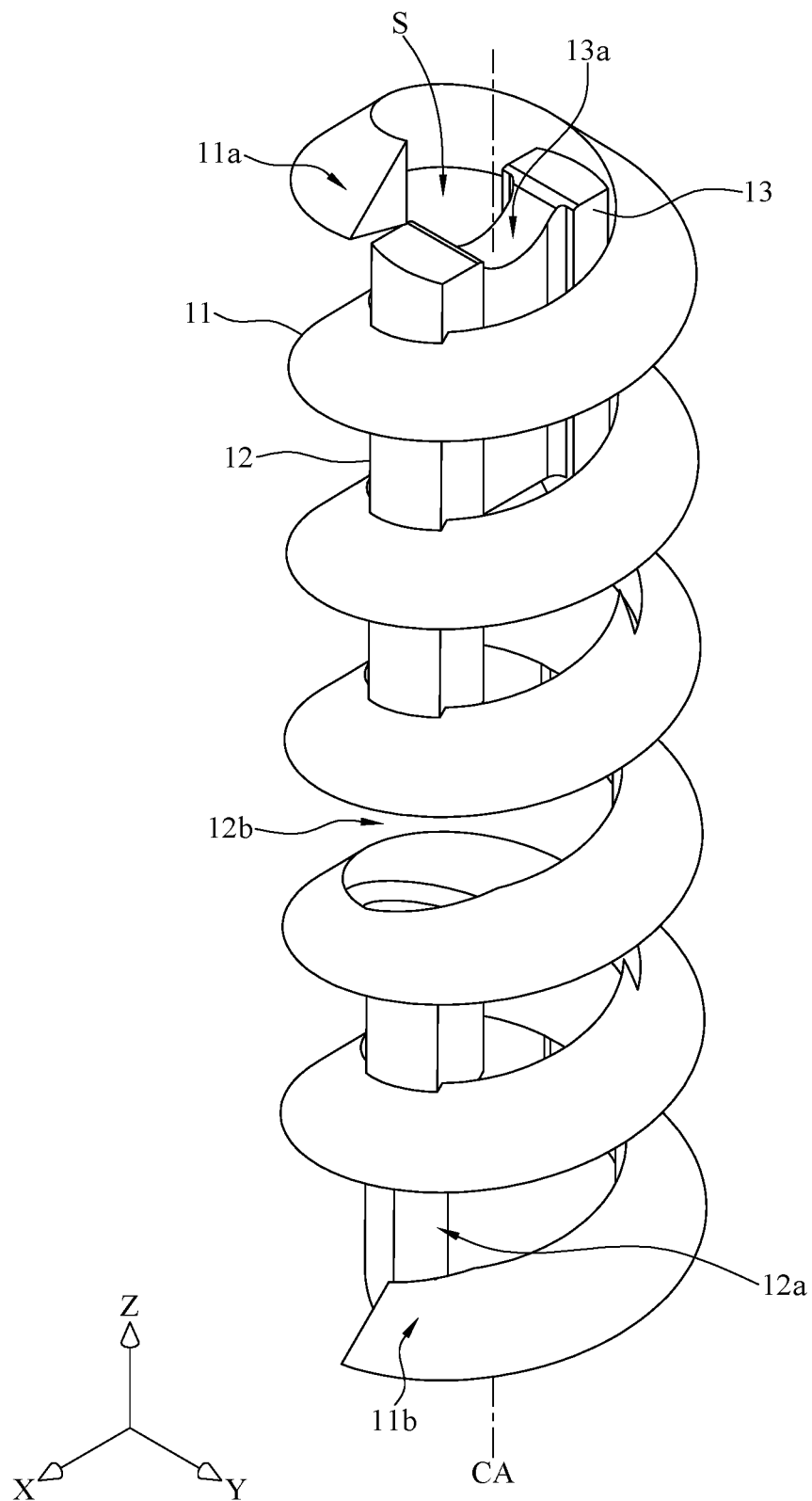
FIG. 1 is a perspective view of a bone implant according to one embodiment of the disclosure.

In the following detailed description, for purposes of explanation, numerous specific details are set forth in order to provide a thorough understanding of the disclosed embodiments. According to detailed description, claims and figures, those having ordinary skill in the art can easily understand the purpose and the advantages of the disclosure and implement it. It will be apparent, however, that one or more embodiments may be practiced without these specific details. In other instances, well-known structures and devices are schematically shown in order to simplify the drawing.

In the figures of the disclosure, the dimensions, ratios, angles, and so on may be exaggerated, but the present disclosure is not limited thereto. Various changes can be made without departing from the purpose of the invention. The orientations mentioned in the description of the embodiments and the figures are for illustration, and the present disclosure is either not limited.

Figure 2:
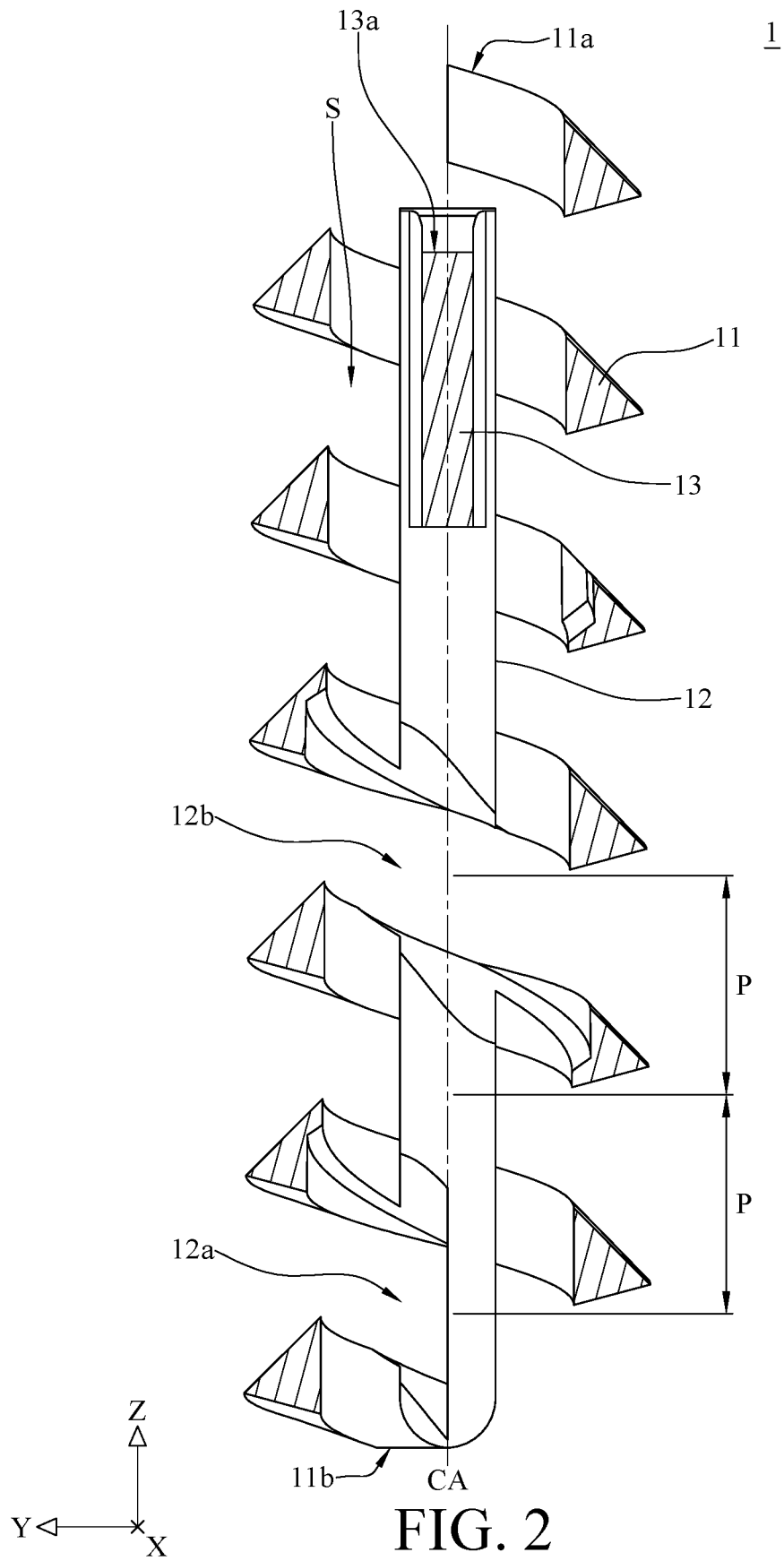
FIG. 2 is a cross-sectional view of the bone implant in FIG. 1.
Figure 3:
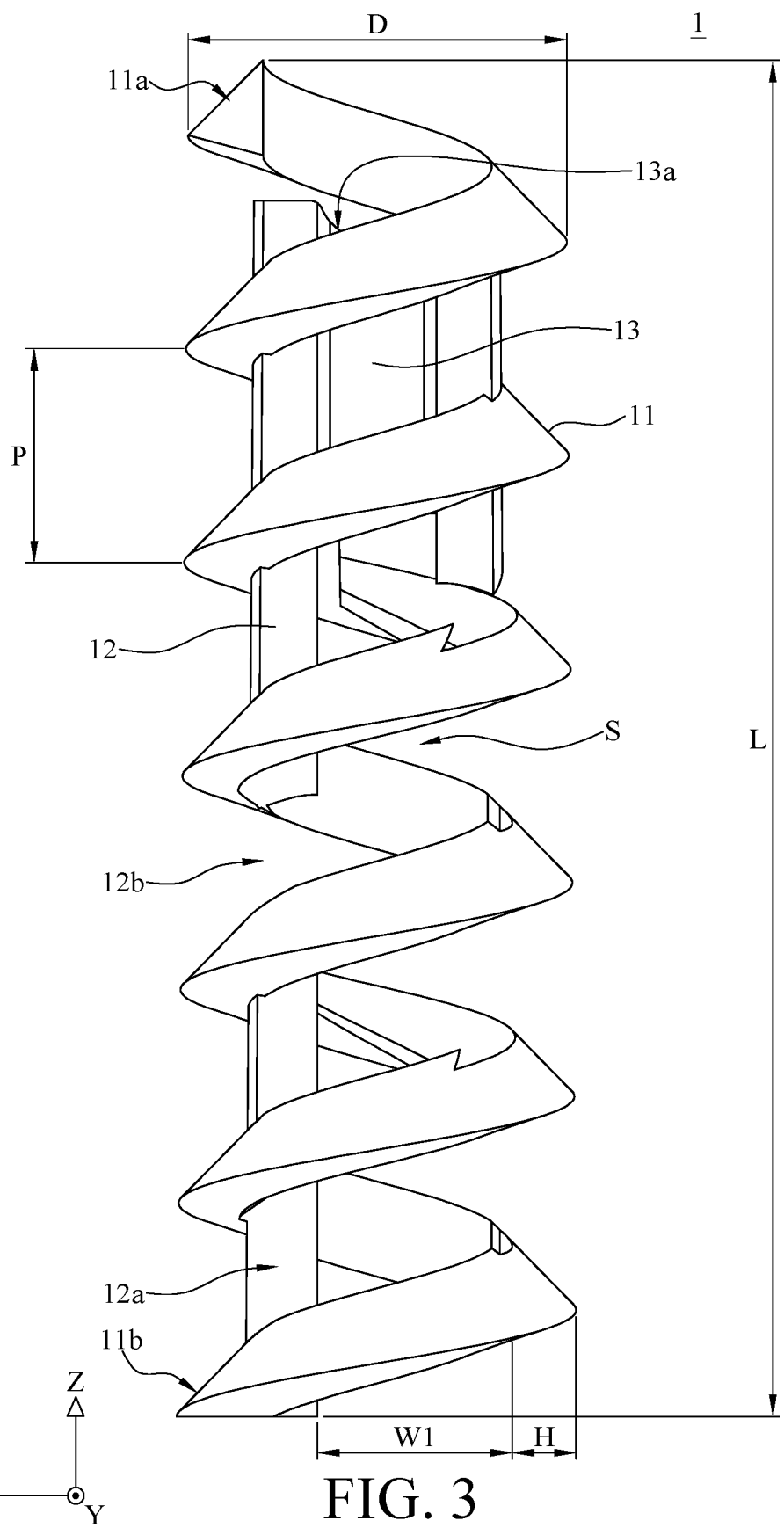
FIG. 3 is a side view of the bone implant in FIG. 1.

Please refer to FIG. 1 to FIG. 3. FIG. 1 is a perspective view of a bone implant according to one embodiment of the disclosure. FIG. 2 is a cross-sectional view of the bone implant in FIG. 1. FIG. 3 is a side view of the bone implant in FIG. 1.

This embodiment provides a bone implant 1. The bone implant 1 may include a helix body 11 and a pillar 12. The helix body 11 surrounds an accommodating space S. The pillar 12 is disposed in the accommodating space S and connected to the helix body 11. The pillar 12 has at least one notch.

In detail, the helix body 11 has two end portions 11a and 11b opposite to each other. The end portion 11a of the helix body 11 is configured to be implanted into human bone prior to the end portion 11b. The accommodating space S is surrounded by the helix body 11 about a central axis CA of the accommodating space S. In more detail, in this embodiment, the helix body 11 may consist of 6 turns, but the present disclosure is not limited thereto. In some other embodiments, the quantity of the turns of the helix body 11 may be modified in a range between 2 and 6 according to actual requirements. The helix body 11 has an outer diameter D, a length L and a thread depth H. In detail, the outer diameter D is a radial diameter of an outermost side of the helix body 11 passing through the central axis CA of the accommodating space S. The length L is an axial length of the helix body 11 measured in a direction parallel to the central axis CA of the accommodating space S. The thread depth H is the thickness of the solid portion of the helix body 11 in the direction perpendicular to the central axis CA of the accommodating space S. In this embodiment, the length L may be about 19.45 mm, the outer diameter D may be about 6 mm, and the thread depth H may be about 1.2 mm, but the present disclosure is not limited thereto. In some other embodiments, the outer diameter D and the length L may have a ratio between about 1 and 1/15. In addition, the helix body 11 is a right-handed helix structure, but the present disclosure is not limited thereto; in some other embodiments, the helix body may be a left-handed helix structure.

A pitch P is a distance between two adjacent crests of the helix body 11 in the direction parallel to the central axis CA. In this embodiment, each turn of the helix body 11 corresponds to a distance in the direction parallel to the central axis CA equal to the pitch P.

The pillar 12 is disposed in the accommodating space S and is inseparably connected to the helix body 11. The one or more notches on the pillar 12 make the pillar 12 partially narrower or divide the pillar 12 in parts. In the embodiment, the pillar 12 may have a narrowing type of notch 12a and a truncated type of notch 12b, and the narrowing type of notch 12a and the truncated type of notch 12b are located in order from the end portion 11b to the end portion 11a of the helix body 11. The narrowing type of notch 12a makes the pillar 12 partially narrower, and the truncated type of notch 12b divides the pillar 12 in parts.

Further, in this embodiment, a distance between a center of the notch 12a and a center of the notch 12b may be equal to two times of the pitch P, but the present disclosure is not limited thereto. In some other embodiments, the pillar 12 may have at least one of the narrowing type of notch 12a and/or the truncated type of notch 12b. In detail, the pillar 12 may have the notch 12a and/or the notch 12b in every one to four pitches P. In the embodiment, the notch 12a and/or the notch 12b may be located closer to the end portion 11b than the end portion 11a, but the present disclosure is not limited thereto. In some other embodiments, the quantities and the arrangement of the narrowing type of notch 12a and the truncated type of notch 12b on the pillar 12 may be modified according to the required flexibility of the bone implant 1. The flexibility of the bone implant 1 may be increased due to the notch 12a and/or the notch 12b.

In this embodiment, the accommodating space S has a minimum width W1 between the pillar 12 and an inner side of the helix body 11 in the radial direction passing through the central axis CA. The minimum width W1 may be about 2.1 mm, but the present disclosure is not limited thereto. In some other embodiments, the minimum width W1 may be more than 0.9 mm according to the size of the tool (not shown in the figures) that is used to screw the bone implant 1 into the human bone. Note that the disclosure is not limited by the tool for screwing the bone implant.

In this embodiment, the bone implant 1 may further include a holding block 13 inseparably connected to the helix body 11 and the pillar 12. The holding block 13 is located inside the helix body 11 and in the end of the pillar 12. The holding block 13 may be located closer to the end portion 11a of the helix body 11 than the end portion 11b of the helix body 11. The holding block 13 has a recess 13a formed near the end portion 11a. The recess 13a is formed on a surface of the holding block 13 facing away from the end portion 11b of the helix body 11.

The bone implant 1 can be made by a 3D printer, a 3D printer and then being sintered, or a laser engraver.

A holding block 13 is adapted to fix a suture (not shown) in position on the bone implant 1. Before the bone implant 1 is implanted into a bone, the suture can be placed into the accommodating space S so as to be looped on the holding block 13 and located at the recess 13a of the holding block 13 so that the suture is fixed on the holding block 13. And then, the tool for screwing the bone implant 1 can be placed into the accommodating space S to clamp the pillar 12 without interfering with the suture. While the tool is being rotated about the central axis CA, the tool rotates the pillar 12 and the helix body 11 to rotate about the central axis CA as well, such that the bone implant 1 is able to be screwed into the bone by the helix body 11.

Figure 4:
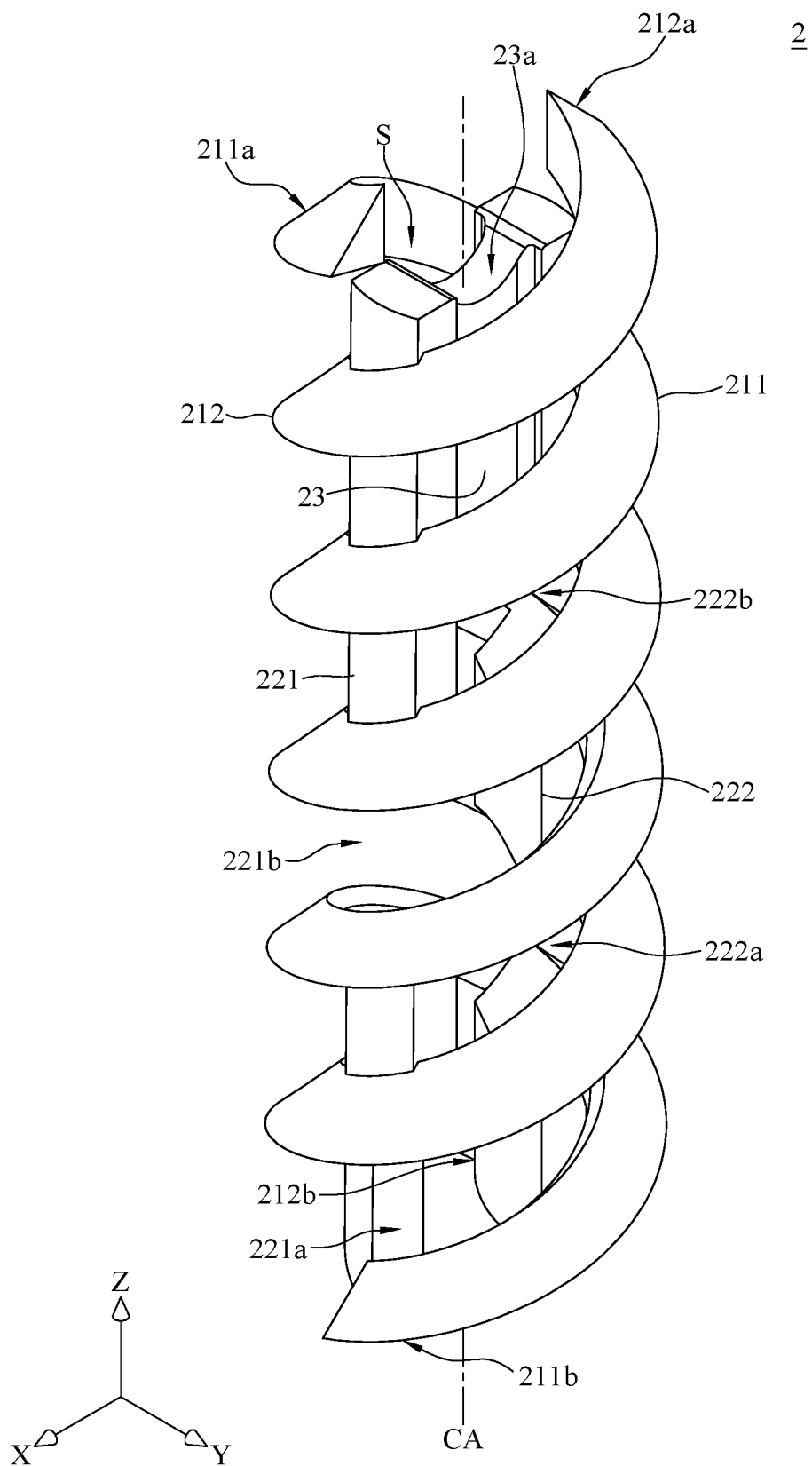
FIG. 4 is a perspective view of a bone implant according to another embodiment of disclosure.
Figure 5:
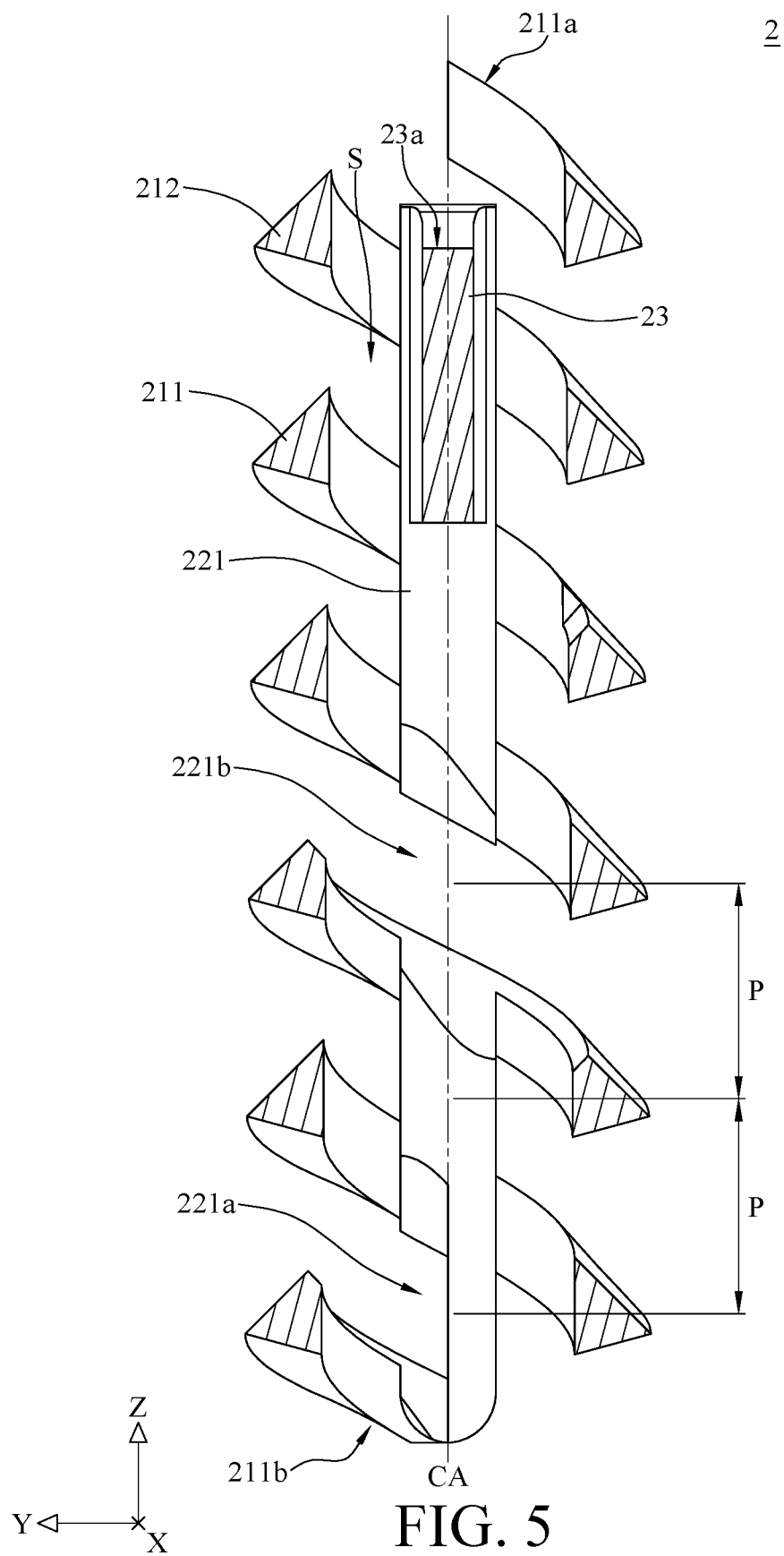
FIG. 5 is a cross-sectional view of the bone implant in FIG. 4.
Figure 6:
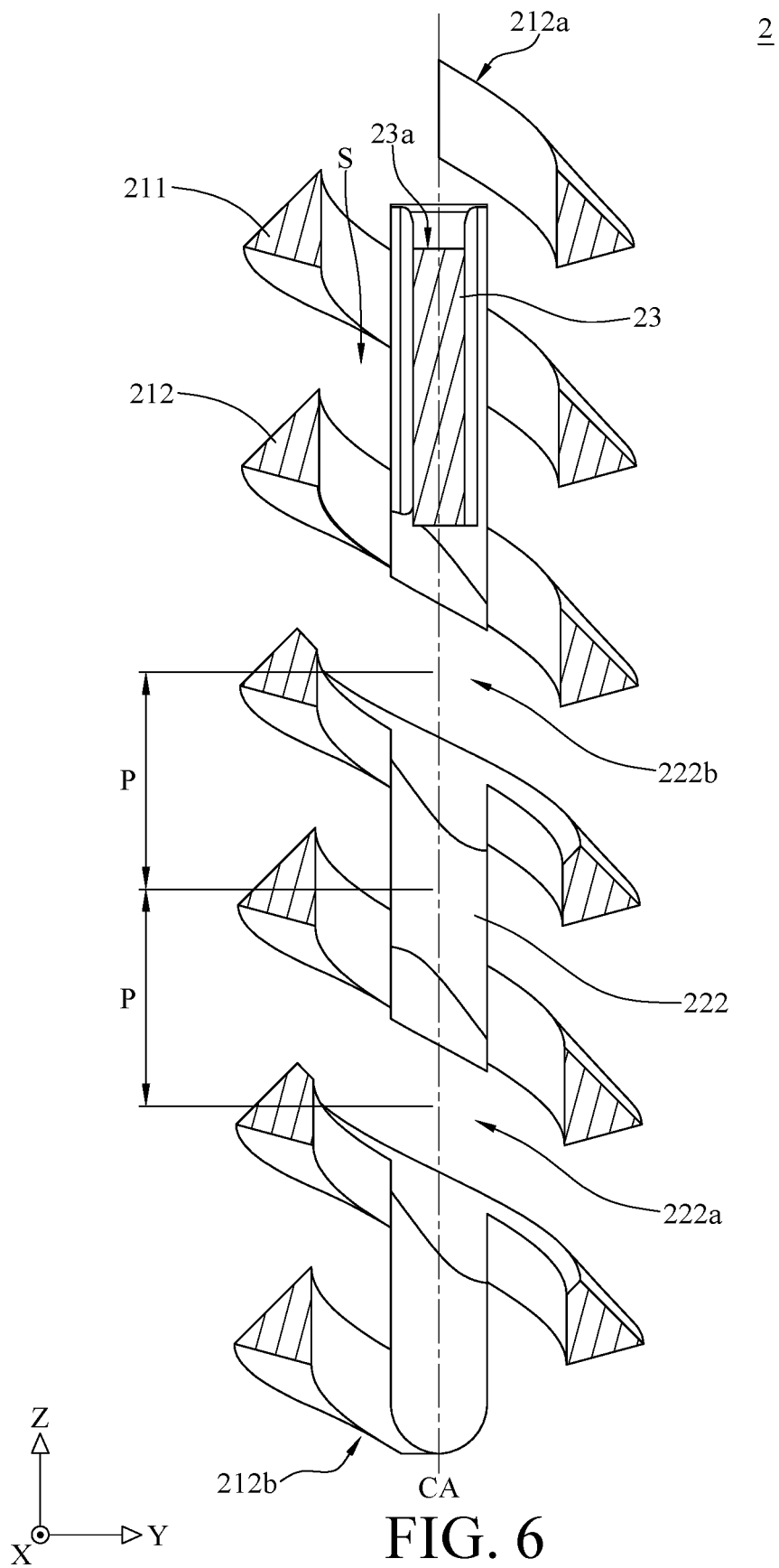
FIG. 6 is another cross-sectional view of the bone implant in FIG. 4.
Figure 7:
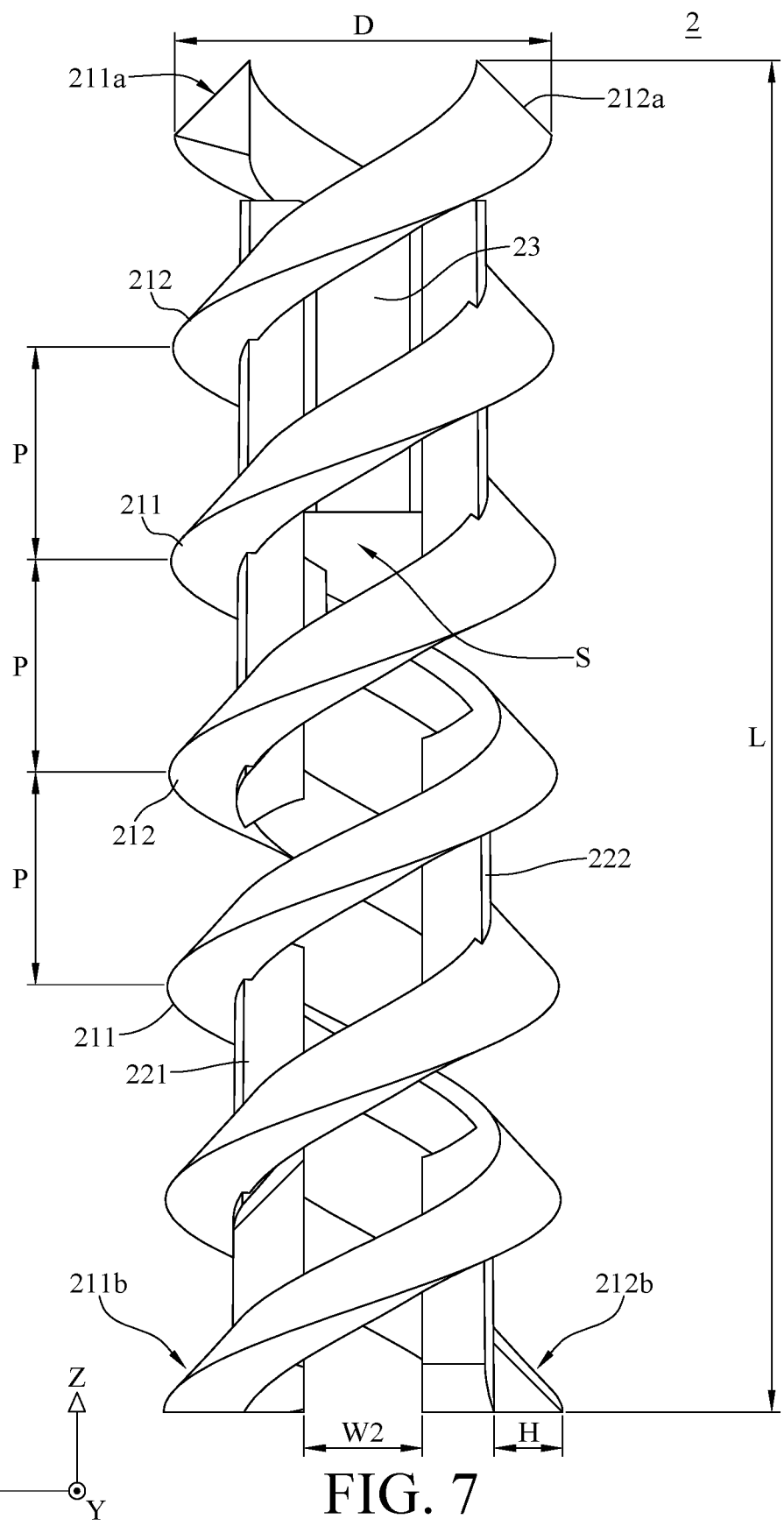
FIG. 7 is a side view of the bone implant in FIG. 4.

Then, please refer to FIG. 4 to FIG. 7. FIG. 4 is a perspective view of a bone implant according to another embodiment of disclosure. FIG. 5 is a cross-sectional view of the bone implant in FIG. 4. FIG. 6 is another cross-sectional view of the bone implant in FIG. 4. FIG. 7 is a side view of the bone implant in FIG. 4.

This embodiment provides a bone implant 2. In this embodiment, the bone implant 2 may include two helix bodies 211 and 212, two pillars 221 and 222 and a holding block 23.

The helix body 211 has two end portions 211a and 211b opposite to each other. The end portion 211a is configured to be implanted into human bone prior to the end portion 211b. The helix body 211 surrounds the accommodating space S spirally about a central axis CA of the accommodating space S. In this embodiment, the helix body 211 may consist of 3 turns, but the present disclosure is not limited thereto. In some other embodiments, the quantity of the turns of the helix body 211 may be modified in a range between 2 to 6 according to actual requirements. In this embodiment, a length L of the helix body 211 may be about 19.45 mm, an outer diameter D of the helix body 211 may be about 6 mm, and a thread depth H of the helix body 211 may be about 1.2 mm, but the present disclosure is not limited thereto. In some other embodiments, the outer diameter D and the length L of the helix body 211 may have a ratio between 1 and 1/15. In this embodiment, the helix body 211 is a right-handed helix structure, but the present disclosure is not limited thereto. In some other embodiments, the helix body may be a left-handed helix structure.

The helix body 212 is similar to the helix body 211. The helix body 212 has two end portion 212a and 212b opposite to each other. The end portion 212a is configured to be implanted into human bone prior to the end portion 212b. In this embodiment, the end portion 211a of the helix body 211 and the end portion 212a of the helix body 212 surround the accommodating space S from different positions and extend with a same direction respectively. In detail, the helix bodies 211 and 212 are radially offset with an angle of about 180 degrees from the central axis CA, and coaxial surround 3 turns about the central axis CA of the accommodating space S respectively. In this embodiment, the quantity of the helix bodies 211 and 212 is two, but it is not restricted. In some other embodiments, the quantity of the helix bodies may be two to four.

A distance between two adjacent turns of the helix bodies 211 and 212 in the direction parallel to the central axis CA is defined as a pitch P. In this embodiment, each turn of the helix body 211 corresponds to a distance in the direction parallel to the central axis CA equal to two times of pitch P, and each turn of the helix body 212 corresponds to a distance in the direction parallel to the central axis CA equal to two times of pitch P.

The pillars 221 and 222 are located at different sides of the central axis CA. In this embodiment, the quantity of the pillars 221 and 222 is two, but it is not restricted.

The pillar 221 is disposed in the accommodating space S and is inseparably connected to the helix bodies 211 and 212. The pillar 221 may have a narrowing type of notch 221a and a truncated type of notch 221b, and the narrowing type of notch 221a and the truncated type of notch 221b are located in order from the end portions 211b and 212b to the end portions 211a and 212a of the pillar 221.

In this embodiment, a distance between a center of the notch 221a and a center of the notch 221b may be equal to two times of pitch P, but the present disclosure is not limited thereto. In some other embodiments, the pillar 221 may have at least one of the narrowing type of notch 221a and the truncated type of notch 221b, and the pillar 221 may have the notch 221a and/or the notch 221b in every one to four pitches P.

The pillar 222 is disposed in the accommodating space S and is inseparably connected to the helix bodies 211 and 212. The pillar 222 may have two truncated type of notches 222a and 222b located in order from the end portions 211b and 212b to the end portions 211a and 212a of the pillar 222.

In this embodiment, a distance between a center of the notch 222a and a center of the notch 222b may be equal to two times of pitch P, but the present disclosure is not limited thereto. In some other embodiments, the pillar 222 may have at least one of the narrowing type of notch and the truncated type of notch, and the pillar 222 may have the narrowing type of notch and/or the truncated type of notch in every one to four pitches P.

In this embodiment, the notches 221a and 221b of the pillar 221 and the notch 222a of the pillar 222 are located closer to the end portions 211b and 212b than the end portions 211a and 212a, and the notch 222b of the pillar 222 is located closer to the end portions 211a and 212a than the end portions 211b and 212b, but the present disclosure is not limited thereto. In some embodiments, the quantities and the arrangement of the notches on the pillars 221 and 222 may be modified according to the required flexibility of the bone implant 2. The flexibility of the bone implant 2 may be increased due to the narrowing type of notch and/or the truncated type of notch on the pillars 221 and/or 222.

In this embodiment, the accommodating space S has a minimum width W2 between the pillars 221 and 222 in a radial direction passing through the central axis CA, and the minimum width W2 may be about 2.1 mm, but the present disclosure is not limited thereto. In some other embodiments, the minimum width W2 may be more than 0.9 mm according to the size of the tool that is used to screw the bone implant 2 into the human bone.

The holding block 23 is located in the accommodating space S and is inseparably connected to the helix bodies 211 and 212 and the pillars 221 and 222. The holding block 23 is located inside the helix bodies 211 and 212 and located in the ends of the pillars 221 and 222. The holding block 23 is located closer to the end portions 211a and 212a than the end portions 211b and 212b. The holding block 23 has a recess 23a formed near the end portions 211a and 212a. The recess 23a is formed on a surface of the holding block 23 facing away from the end portions 211b and 212b of the helix bodies 211 and 212.

The bone implant 2 can be made by a 3D printing printer, a 3D printer and then being sintered or a laser engraver.

Before the bone implant 2 is implanted into bone, a suture can be placed into the accommodating space S so as to be looped on the holding block 23 and located at the recess 23a of the holding block 23 so that the suture is fixed on the holding block 23. And then, the tool for screwing the bone implant 2 is placed into the accommodating space S to clamp the pillars 221 and 222 without interfering with the suture. While the tool is being rotated about the central axis CA, the tool rotates the pillars 221 and 222 and the helix bodies 211 and 212 to rotate about the central axis CA as well, such that the bone implant 2 is able to be screwed into the bone by the helix bodies 211 and 212.

Figure 8:
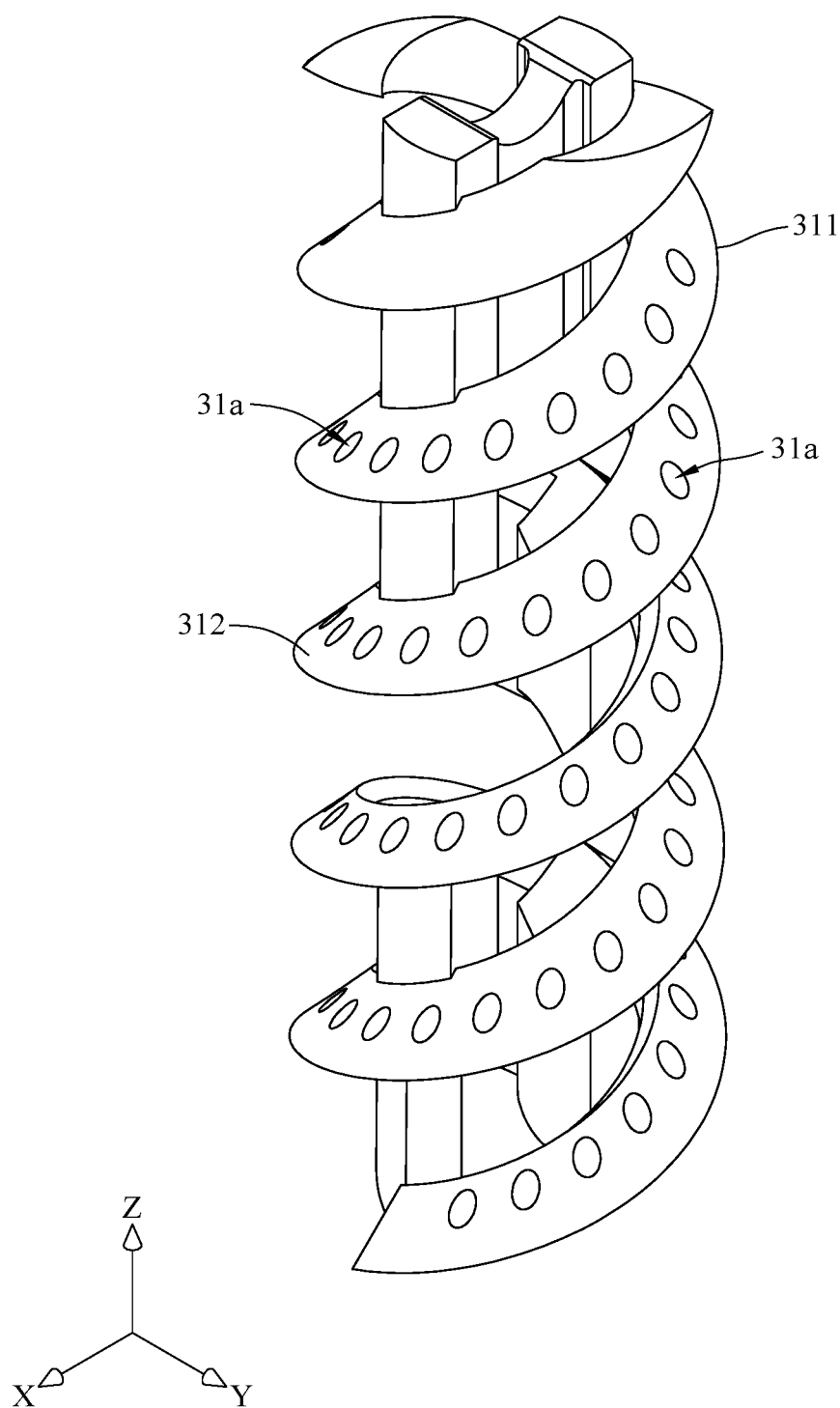
FIG. 8 is a perspective view of a bone implant according to still another embodiment of the disclosure.

Please refer to FIG. 8. FIG. 8 is a perspective view of a bone implant according to still another embodiment of the disclosure. This embodiment provides a bone implant 3, and the bone implant 3 is similar to the bone implant 2 in FIG. 4.

It is noted that each of helix bodies 311 and 312 of the bone implant 3 has a plurality of holes 31a. After the bone implant 3 has been implanted into bone, osteoblast is allowed to grow bone in the holes 31a so as to improving bonding strength. In addition, in the case that the bone implant 3 is made of a degradable material, the holes 31a of the bone implant 3 can increase the contact areas between the bone and the bone implant 3, thereby improving the efficiency in degrading the bone implant 3.

The following introduces a plurality of bone implants similar to the bone implant 3 in FIG. 8 with unchanged parameters in the quantities of the pillars, the quantities of the notches, the pitch quantities of the distances between the notches, the quantities of the helix bodies, the outer diameters of the helix bodies, the lengths of the helix bodies, and the thread depths of the helix bodies. Compare with the maximum axial displacements of the bone implants in the central axis CA in different amount of turns. The larger displacement of the bone implant in the central axis CA, the greater flexibility. The results are shown in Table 1.

TABLE 1

| amount of turns | maximum axial displacement (mm) |
| --- | --- |
| 3 | 0.145 |
| 3.25 | 0.156 |
| 3.5 | 0.2629 |
| 3.75 | 0.3152 |
| 4 | 0.08418 |
| 4.25 | 0.09298 |

It can be seen that the bone implants with the helix bodies in 3.5 and 3.75 turns have larger maximum axial displacements than the others and thus having greater flexibility.

Figure 9:
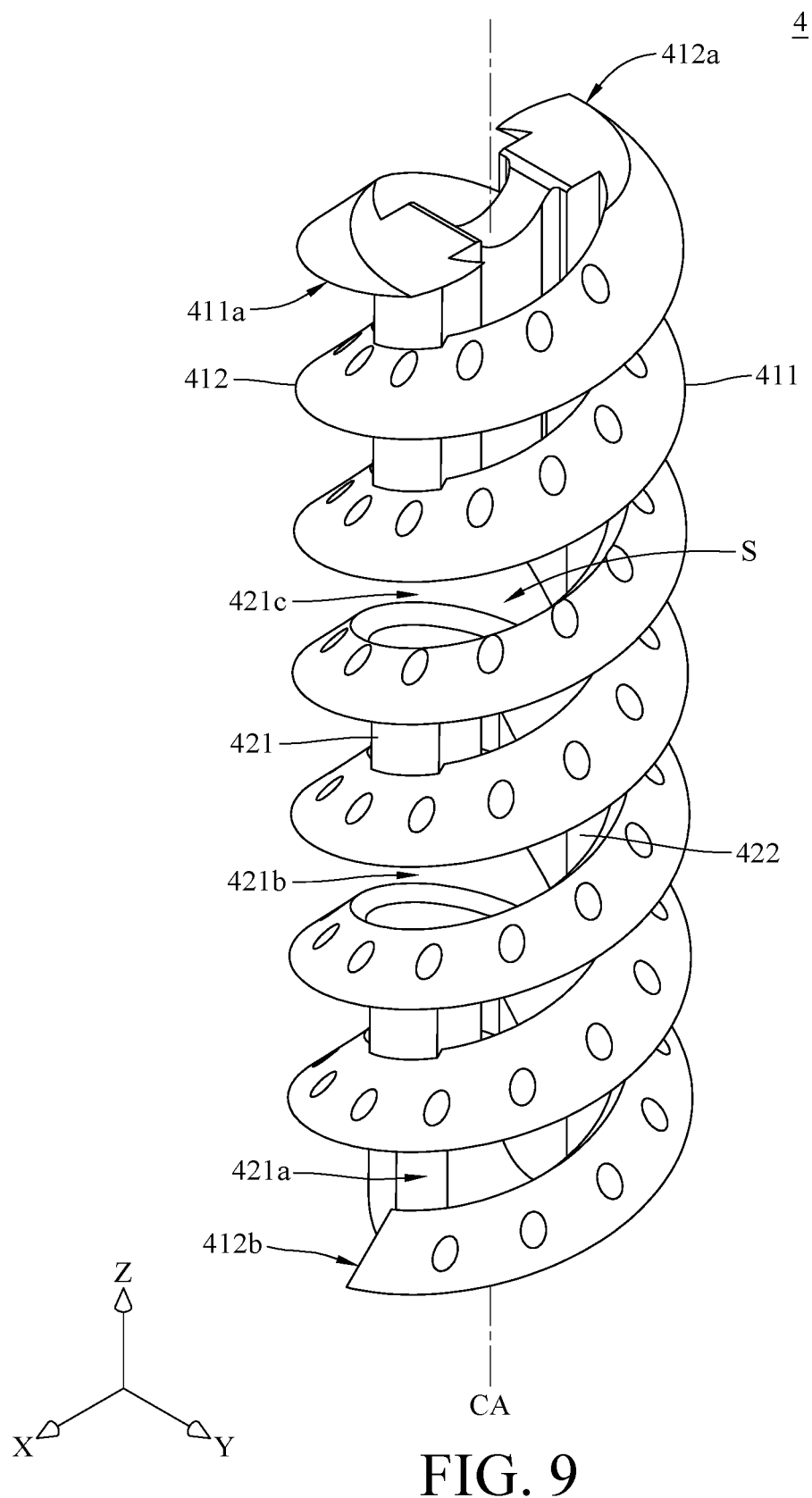
FIG. 9 is a perspective view of a bone implant according to yet another embodiment of the disclosure.
Figure 10:
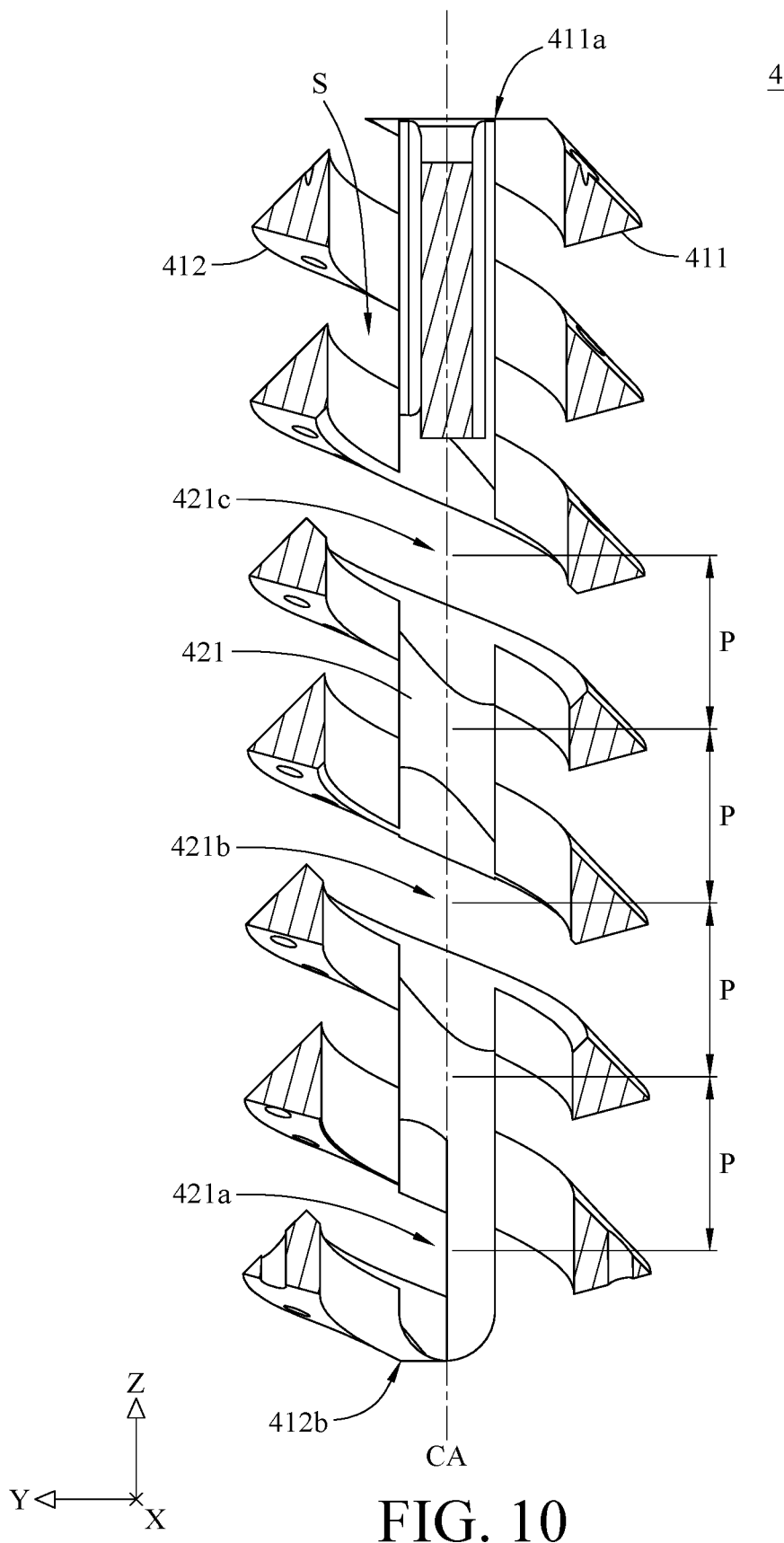
FIG. 10 is a cross-sectional view of the bone implant in FIG. 9.
Figure 11:
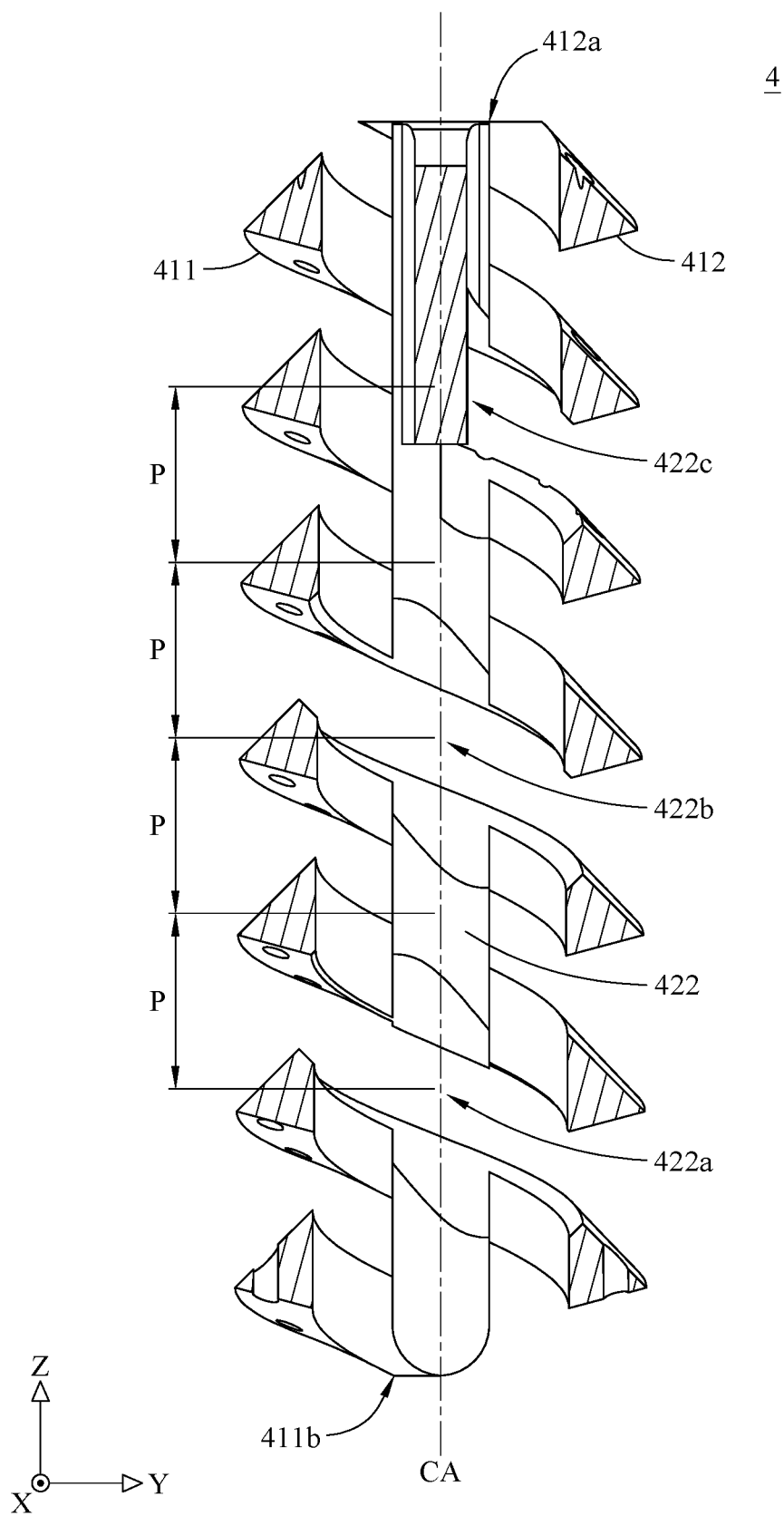
FIG. 11 is another cross-sectional view of the bone implant in FIG. 9.

Please refer to FIG. 9 to FIG. 11. FIG. 9 is a perspective view of a bone implant according to yet another embodiment of the disclosure. FIG. 10 is a cross-sectional view of the bone implant in FIG. 9. FIG. 11 is another cross-sectional view of the bone implant in FIG. 9. This embodiment provides a bone implant 4, and the bone implant 4 is similar to the bone implant 3 in FIG. 8.

It is noted that, in this embodiment, the bone implant 4 has two helix bodies 411 and 412 surrounded an accommodating space S about a central axis CA. Each of the helix bodies 411 and 412 consists of 3.5 turns.

In this embodiment, the pillar 421 is disposed in the accommodating space S and is inseparably connected to the helix bodies 411 and 412. The pillar 421 may have a narrowing type of notch 421*a* and two truncated type of notches 421*b* and 421*c*, and the narrowing type of notch 421*a* and the truncated type of notches 421*b* and 421*c* are located in order from the end portions 411*b* and 412*b* to the end portions 411*a* and 412*a*. A distance between a center of the notch 421*a* and a center of the notch 421*b* may be equal to two times of pitch P, and the distance between a center of the notch 421*b* and a center of the notch 421*c* may be equal to two times of pitch P, but the present disclosure is not limited thereto.

In this embodiment, the pillar 422 is disposed in the accommodating space S and is inseparably connected to the helix bodies 411 and 412. The pillar 422 may have two truncated type of notches 422*a* and 422*b* and a narrowing type of notch 422*c*, and the truncated type of notches 422*a* and 422*b* and the narrowing type of notch 422*c* are located in order from the end portions 411*b* and 412*b* to the end portions 411*a* and 412*a*. A distance between a center of the notch 422*a* and a center of the notch 422*b* may be equal to two times of pitch P, and a distance between the center of the notch 422*b* and a center of the notch 422*c* may be equal to two times of pitch P, but the present disclosure is not limited thereto.

In this embodiment, the notches 421*a* and 421*b* of the pillar 421 and the notch 422*a* of the pillar 422 are located closer to the end portions 411*b* and 412*b* than the end portions 411*a* and 412*a*. The notch 422*b* is located close to center portions of the helix bodies 411 and 412. The notches 421*c* and 422*c* are located closer to the end portions 411*a* and 412*a* than the end portions 411*b* and 412*b*, but the present disclosure is not limited thereto. In other embodiments, the quantities and the arrangement of the notches on the pillars 421 and 422 may be modified according to the required flexibility of the bone implant 4. The flexibility of the bone implant 4 may be increased due to the narrowing type of notches and/or the truncated type of notches on the pillars 421 and/or 422.

Figure 12:
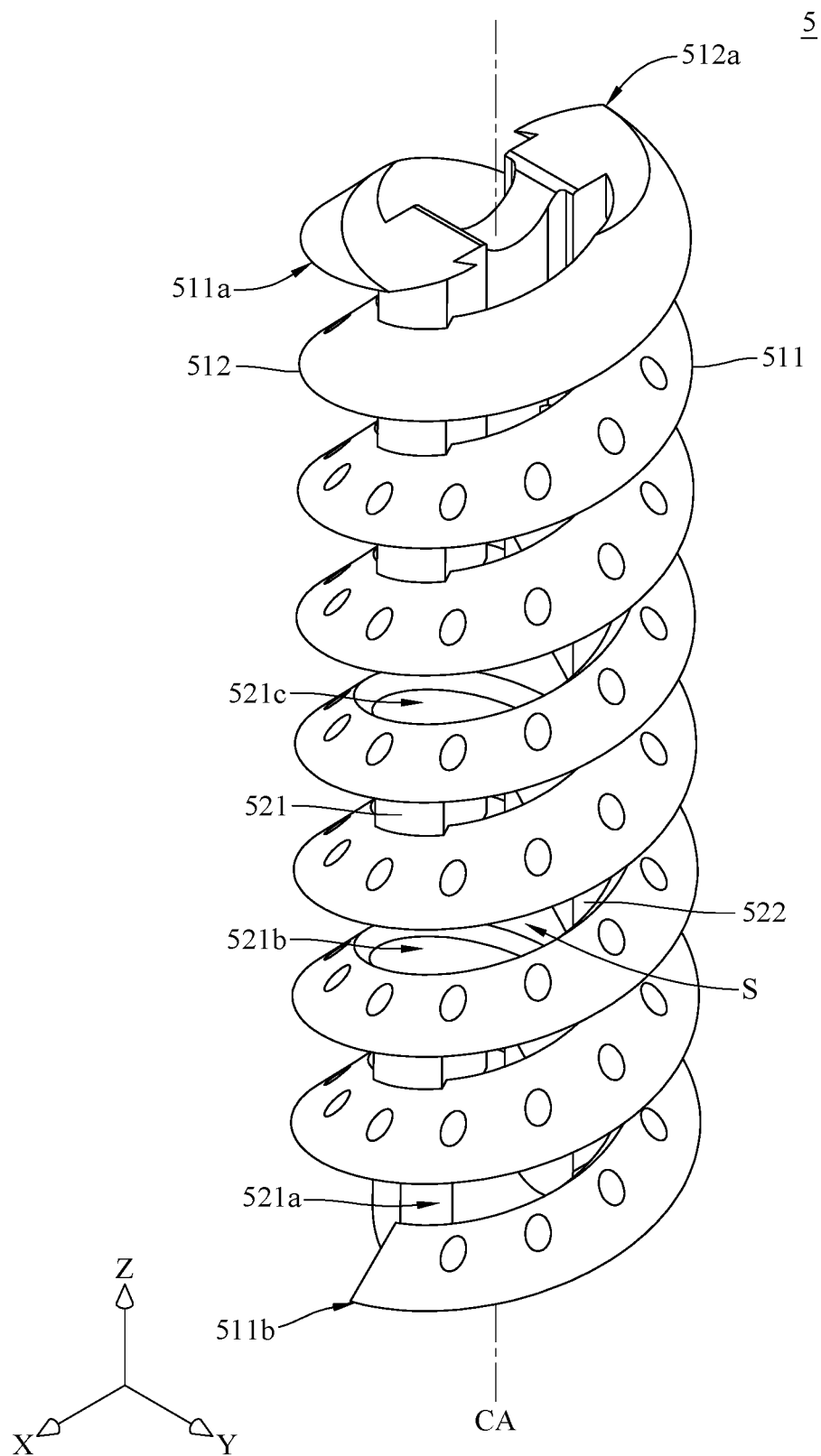
FIG. 12 is a perspective view of a bone implant according to still yet another embodiment of the disclosure.
Figure 13:
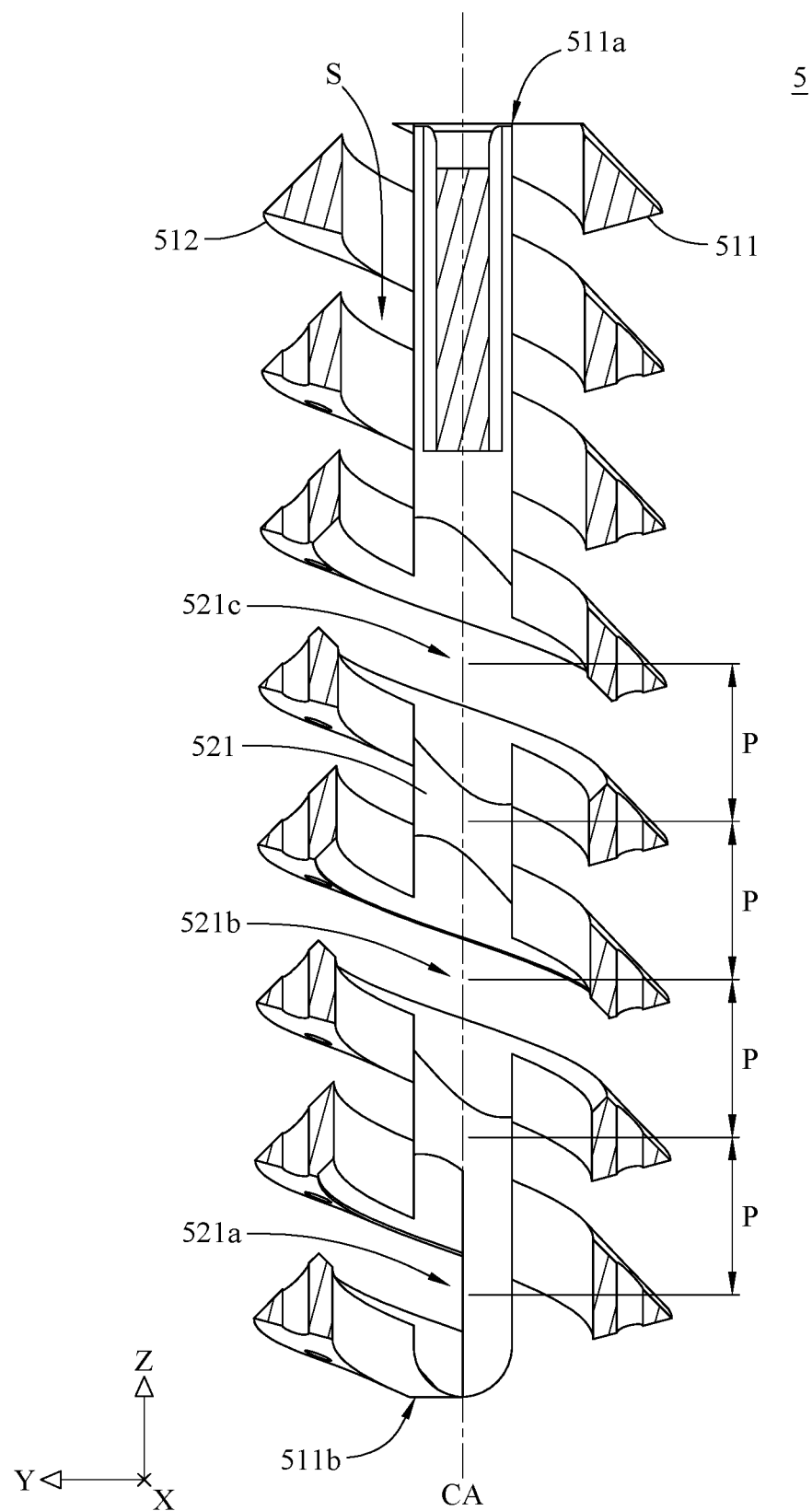
FIG. 13 is a cross-sectional view of the bone implant in FIG. 12.
Figure 14:
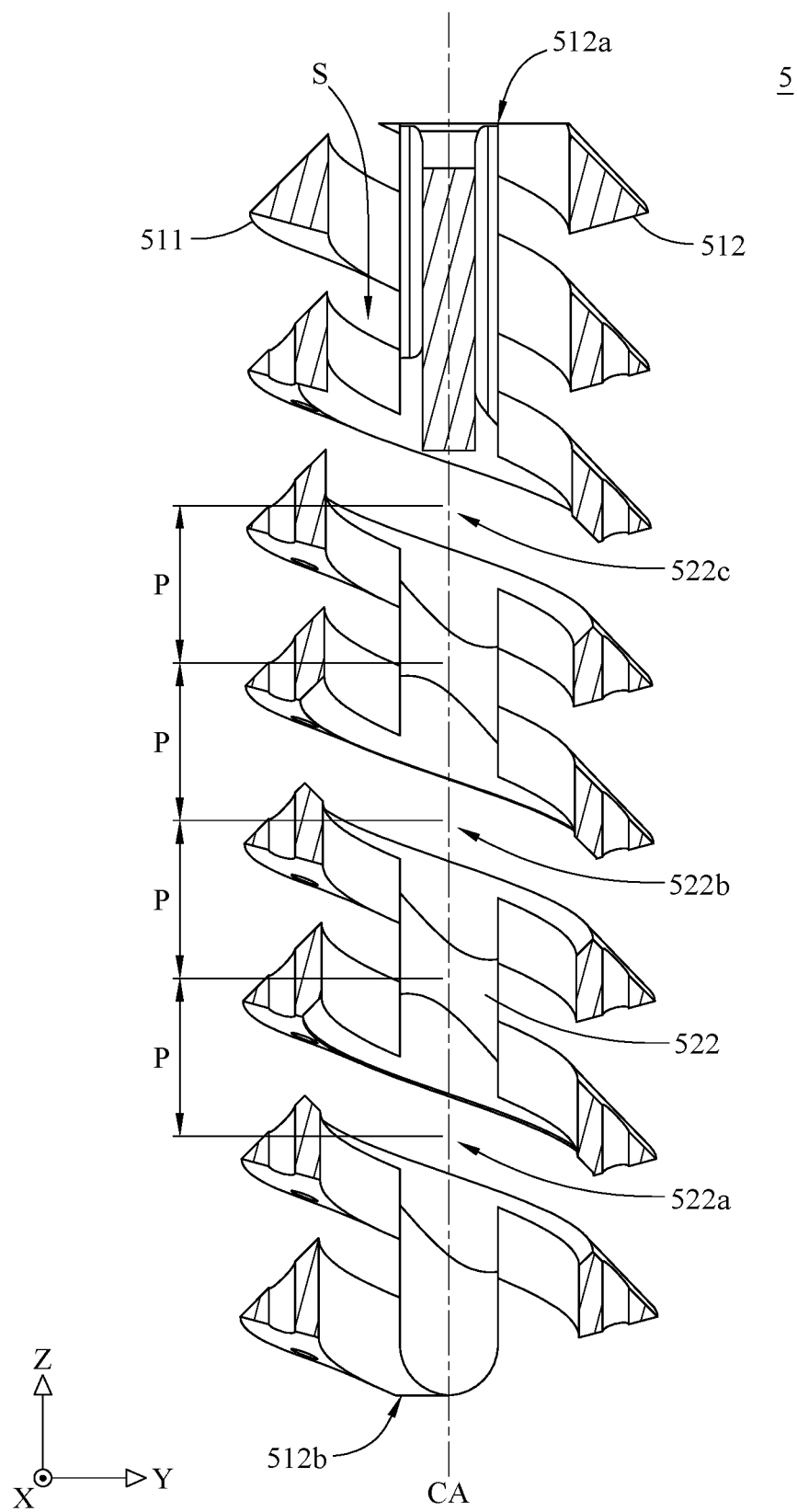
FIG. 14 is another cross-sectional view of the bone implant in FIG. 12.

Please refer to FIG. 12 to FIG. 14. FIG. 12 is a perspective view of a bone implant according to still yet another embodiment of the disclosure. FIG. 13 is a cross-sectional view of the bone implant in FIG. 12. FIG. 14 is another cross-sectional view of the bone implant in FIG. 12. This embodiment provides a bone implant 5, and the bone implant 5 is similar to the bone implant 3 in FIG. 8.

It is noted that, in this embodiment, the bone implant 5 has two helix bodies 511 and 512 surrounded an accommodating space S about a central axis CA. Each of the helix bodies 511 and 512 consists of 4 turns.

In this embodiment, the pillar 521 is disposed in the accommodating space S and is inseparably connected to the helix bodies 511 and 512. The pillar 521 may have a narrowing type of notch 521*a* and two truncated type of notches 521*b* and 521*c*, and the narrowing type of notch 521*a* and the truncated type of notches 521*b* and 521*c* are located in order from the end portions 511*b* and 512*b* to the end portions 511*a* and 512*a*. A distance between a center of the notch 521*a* and a center of the notch 521*b* may be equal to two times of pitch P, and a distance between the center of the notch 521*b* and a center of the notch 521*c* may be equal to two times of pitch P, but the present disclosure is not limited thereto.

In this embodiment, the pillar 522 is disposed in the accommodating space S and is inseparably connected to the helix bodies 511 and 512. The pillar 522 may have three truncated type of notches 522*a*, 522*b* and 522*c*, and the truncated type of notches 522*a*, 522*b* and 522*c* are located in order from the end portions 511*b* and 512*b* to the end portions 511*a* and 512*a*. A distance between a center of the notch 522*a* and a center of the notch 522*b* may be equal to two times of pitch P, and a distance between the center of the notch 522*b* and a center of the notch 522*c* may be equal to two times of pitch P, but the present disclosure is not limited thereto.

In this embodiment, the notches 521*a* and 521*b* of the pillar 521 and the notches 522*a* and 522*b* of the pillar 522 are located closer to the end portions 511*b* and 512*b* than the end portions 511*a* and 512*a*. The notches 521*c* and 522*c* are located closer to the end portions 511*a* and 512*a* than the end portions 511*b* and 512*b*, but the present disclosure is not limited thereto. In other embodiments, the quantities and the arrangement of the notches on the pillars 521 and 522 may be modified according to the required flexibility of the bone implant 5. The flexibility of the bone implant 5 may be increased due to the narrowing type of notches and/or the truncated type of notches on the pillars 521 and/or 522.

Figure 15:
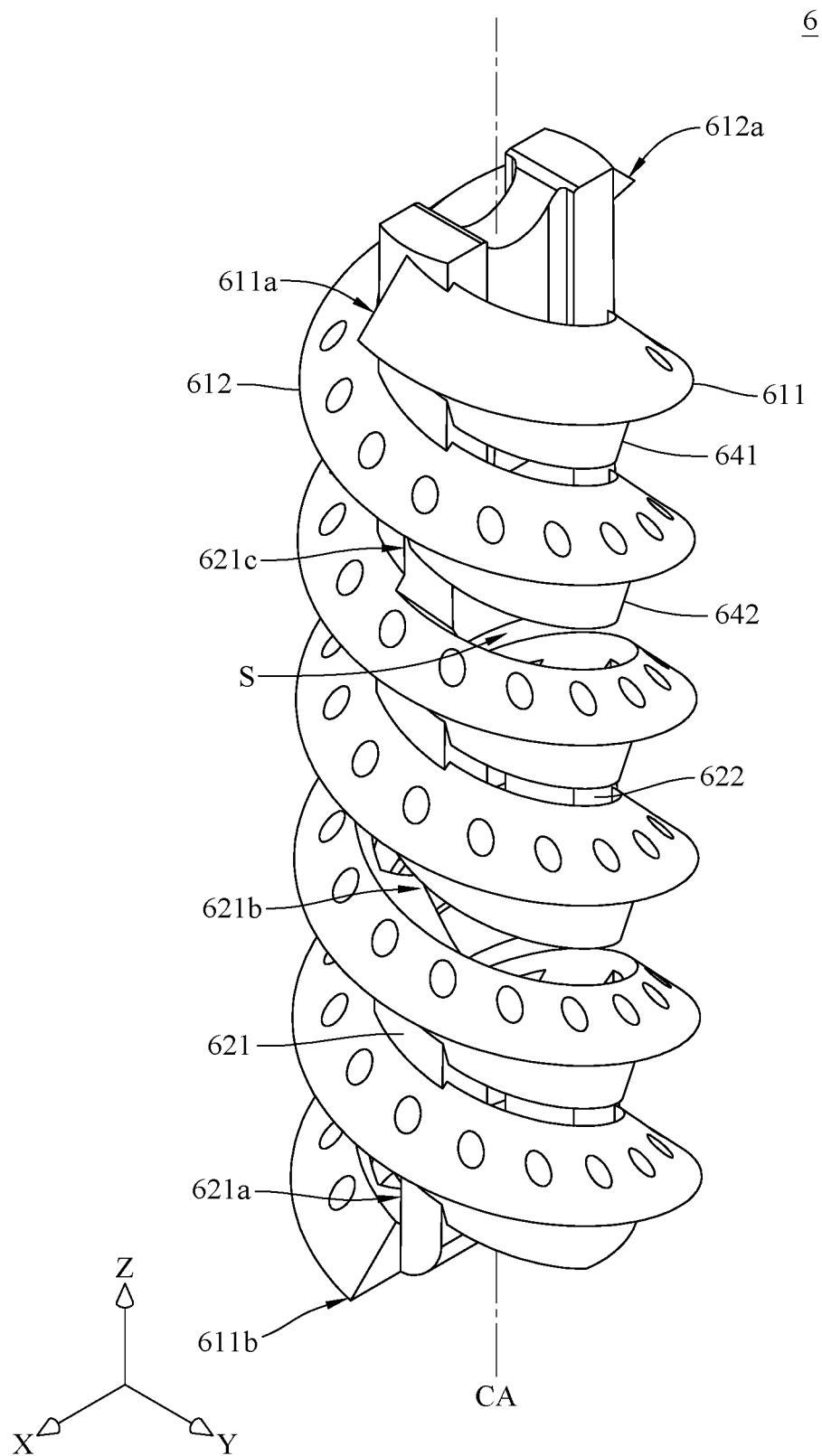
FIG. 15 is a perspective view of a bone implant according to still yet further another embodiment of the disclosure.
Figure 16:
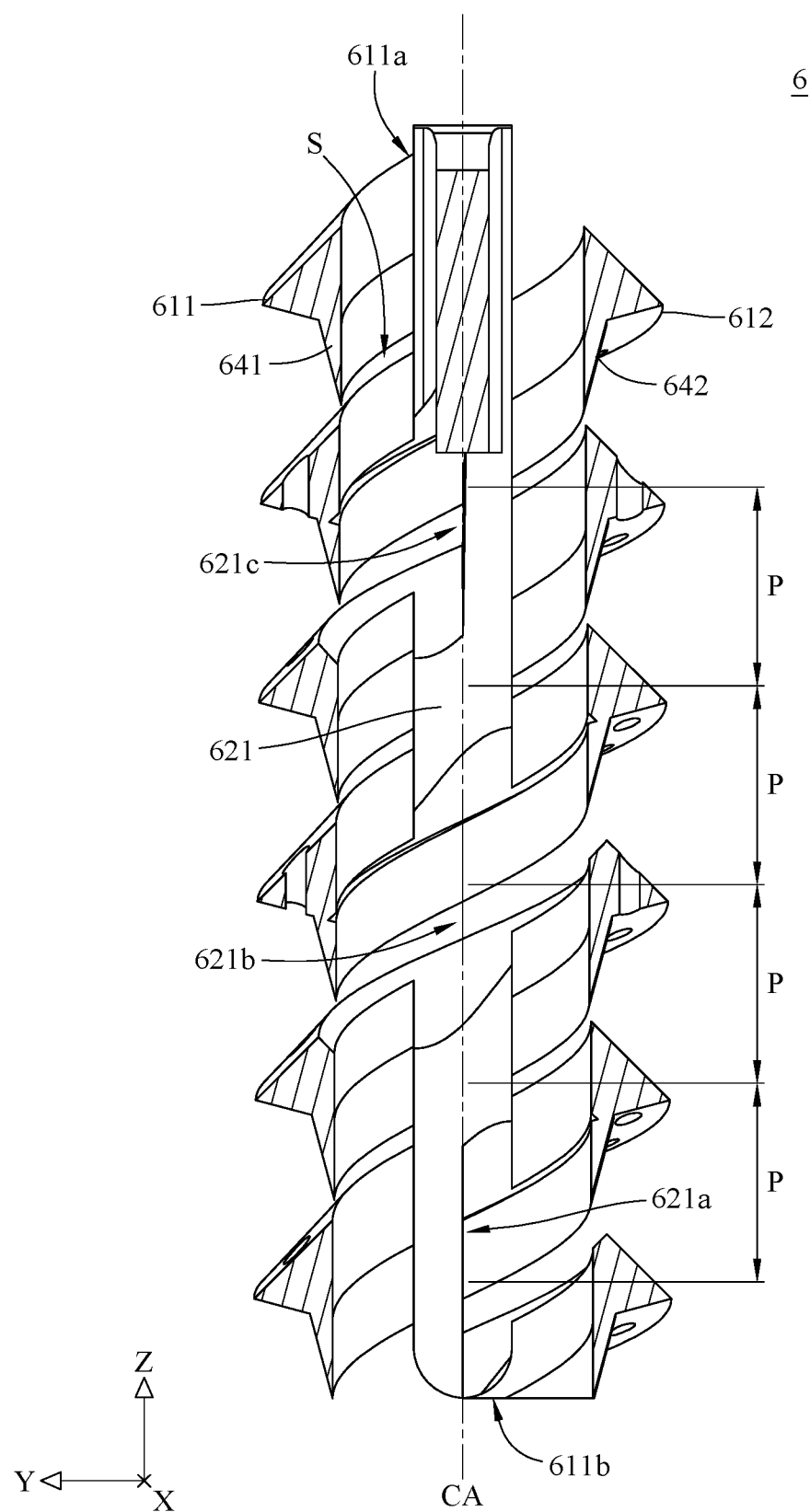
FIG. 16 is a cross-sectional view of the bone implant in FIG. 15.
Figure 17:
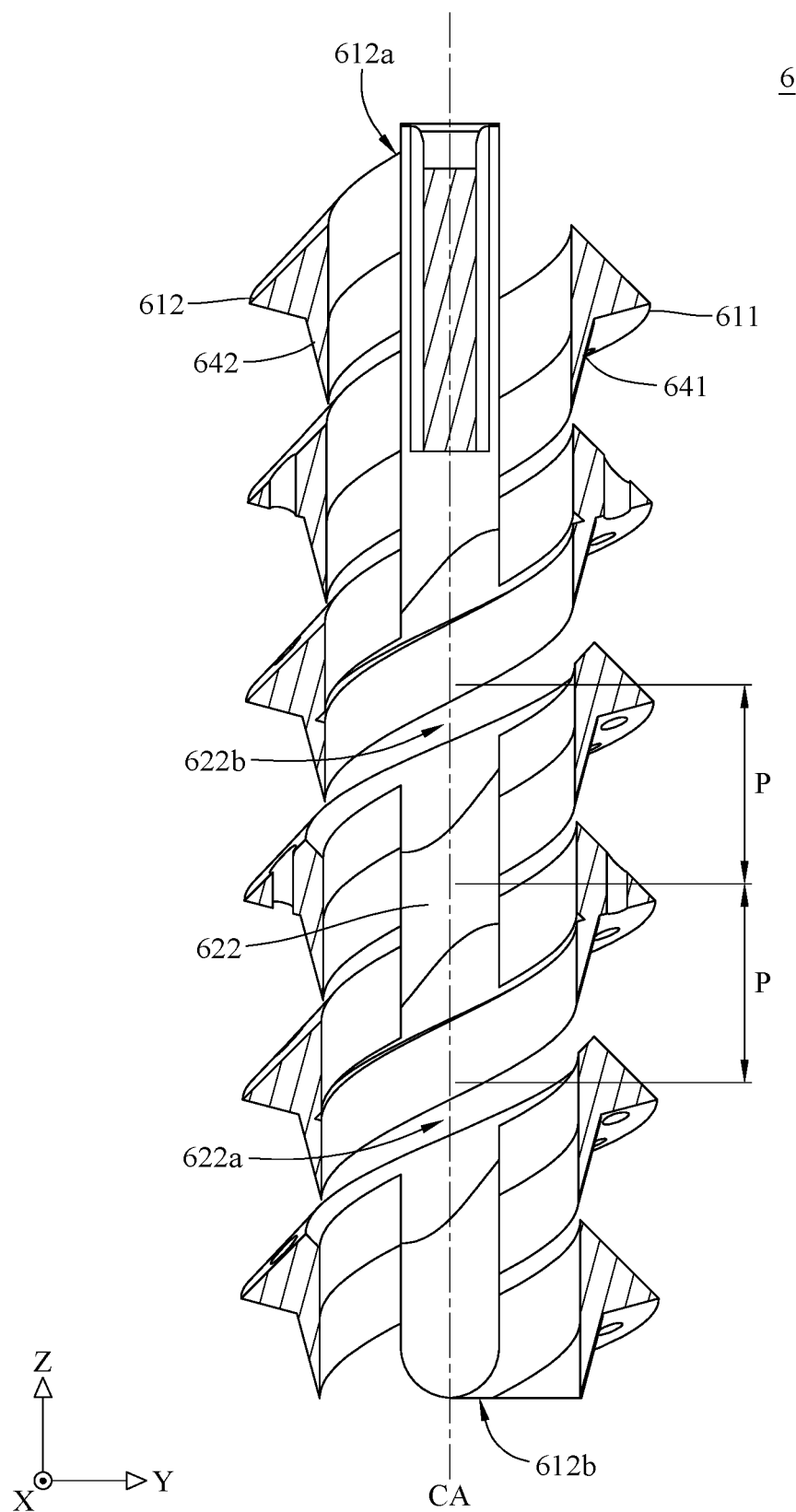
FIG. 17 is another cross-sectional view of the bone implant in FIG. 15.

Then, please refer to FIG. 15 to FIG. 17. FIG. 15 is a perspective view of a bone implant according to still yet further another embodiment of the disclosure. FIG. 16 is a cross-sectional view of the bone implant in FIG. 15. FIG. 17 is another cross-sectional view of the bone implant in FIG. 15. This embodiment provides a bone implant 6, and the bone implant 6 is similar to the bone implant 3 in FIG. 8.

It is noted that, in this embodiment, the bone implant 6 has two helix bodies 611 and 612 surrounded an accommodating space S about a central axis CA. In this embodiment, each of the two helix bodies 611 and 612 is a left-handed helix structure, but the present disclosure is not limited thereto.

In this embodiment, the pillar 621 is disposed in the accommodating space S and is inseparably connected to the two helix bodies 611 and 612. The pillar 621 may have a narrowing type of notch 621*a*, a truncated type of notch 621*b* and a narrowing type of notch 621*c* located in order from the end portions 611*b* and 612*b* to the end portions 611*a* and 612*a*. A distance between a center of the notch 621*a* and a center of the notch 621*b* may be equal to two times of pitch P, and a distance between the center of the notch 621*b* and a center of the notch 621*c* may be equal to two times of pitch P, but the present disclosure is not limited thereto.

In this embodiment, the pillar 622 is disposed in the accommodating space S and is inseparably connected to the helix bodies 611 and 612. The pillar 622 may have two truncated type of notches 622*a* and 622*b* located in order from the end portions 611*b* and 612*b* to the end portions 611*a* and 612*a*. A distance between a center of the notch 621*a* and a center of the notch 421*b* may be equal to two times of pitch P, but the present disclosure is not limited thereto.

In this embodiment, the notches 621*a* and 621*b* of the pillar 621 and the notch 622*a* of the pillar 622 are located closer to the end portions 611*b* and 612*b* than the end portions 611*a* and 612*a*. The notches 621*c* and 622*b* are located closer to the end portions 611*a* and 612*a* than the end portions 611*b* and 612*b*, but the present disclosure is not limited thereto. In other embodiments, the quantities and the arrangement of the notches on the pillars 621 and/or 622 may be modified according to the required flexibility of the bone implant 6. The flexibility of the bone implant 6 may be increased due to the narrowing type of notches and/or the truncated type of notches on the pillars 621 and/or 622.

In this embodiment, the bone implant 6 may further include walls 641 and 642. The wall 641 is inseparably connected to the helix body 611 and surrounds the accommodating space S with the helix body 611. The wall 641 extends from the helix body 611 in the direction parallel to the central axis CA. The wall 642 is inseparably connected to the helix body 612 and surrounds the accommodating space S with the helix body 612. The wall 642 extends from the helix body 612 in the direction parallel to the central axis CA. When the bone implant 6 is implanted into bone, the walls 641 and 642 of the bone implant 6 can increase the contact area between the bone and the bone implant 6.

In this embodiment, the walls 641 and 642 has no hole, but the present disclosure is not limited thereto. In some other embodiments, each of the walls 641 and 642 may have a plurality of holes. In such a case, after the bone implant 6 has been implanted into bone, osteoblast is allowed to grow bone in the holes so as to improve bonding strength. In addition, in the case that the bone implant 6 is made of a degradable material, the holes of the wall 641 and 642 can increase the contact areas between the bone and the bone implant 6, thereby improving the efficiency in degrading the bone implant 6.

Figure 18:
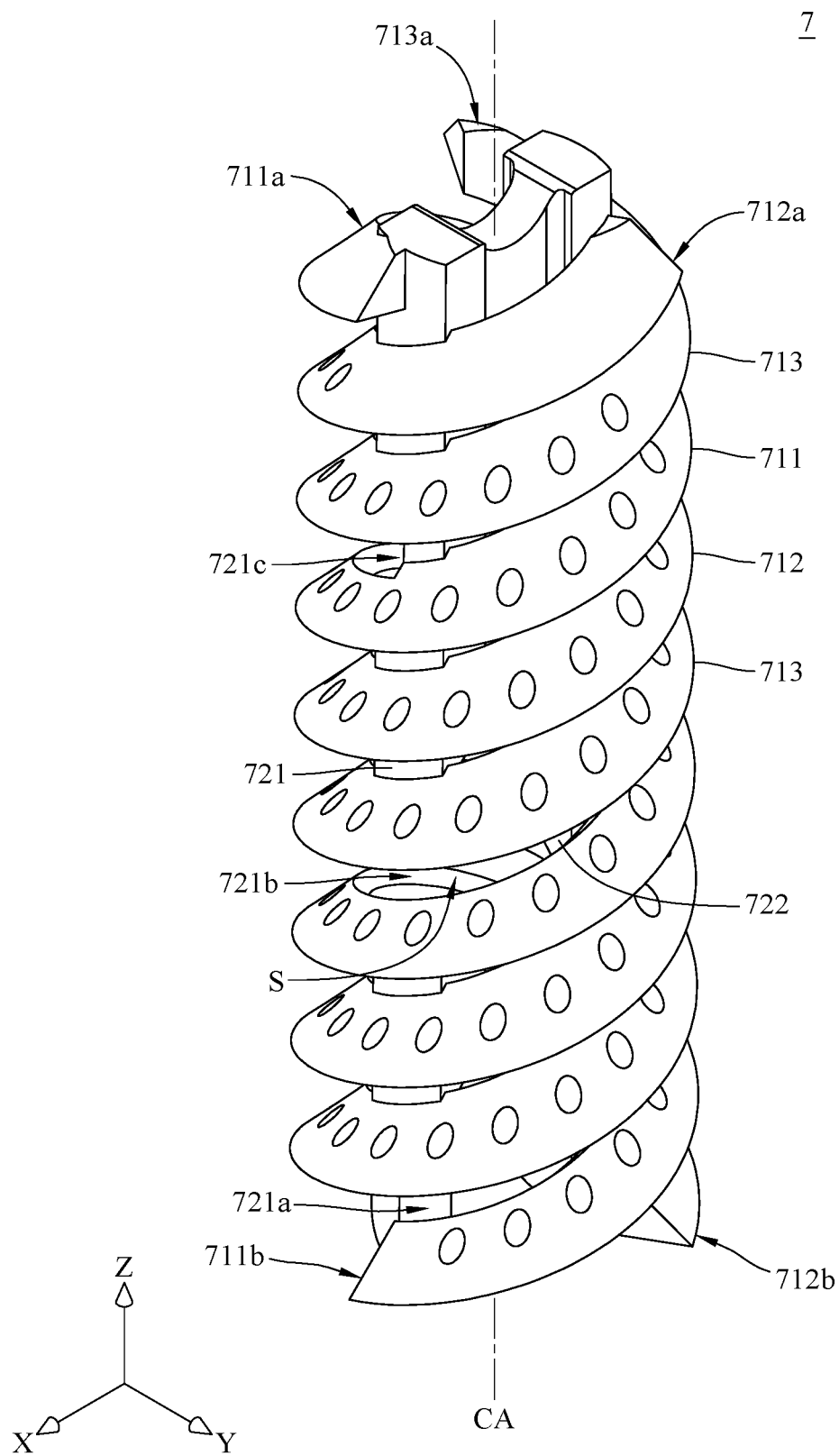
FIG. 18 is a perspective view of a bone implant according to still a further embodiment of the disclosure.
Figure 19:
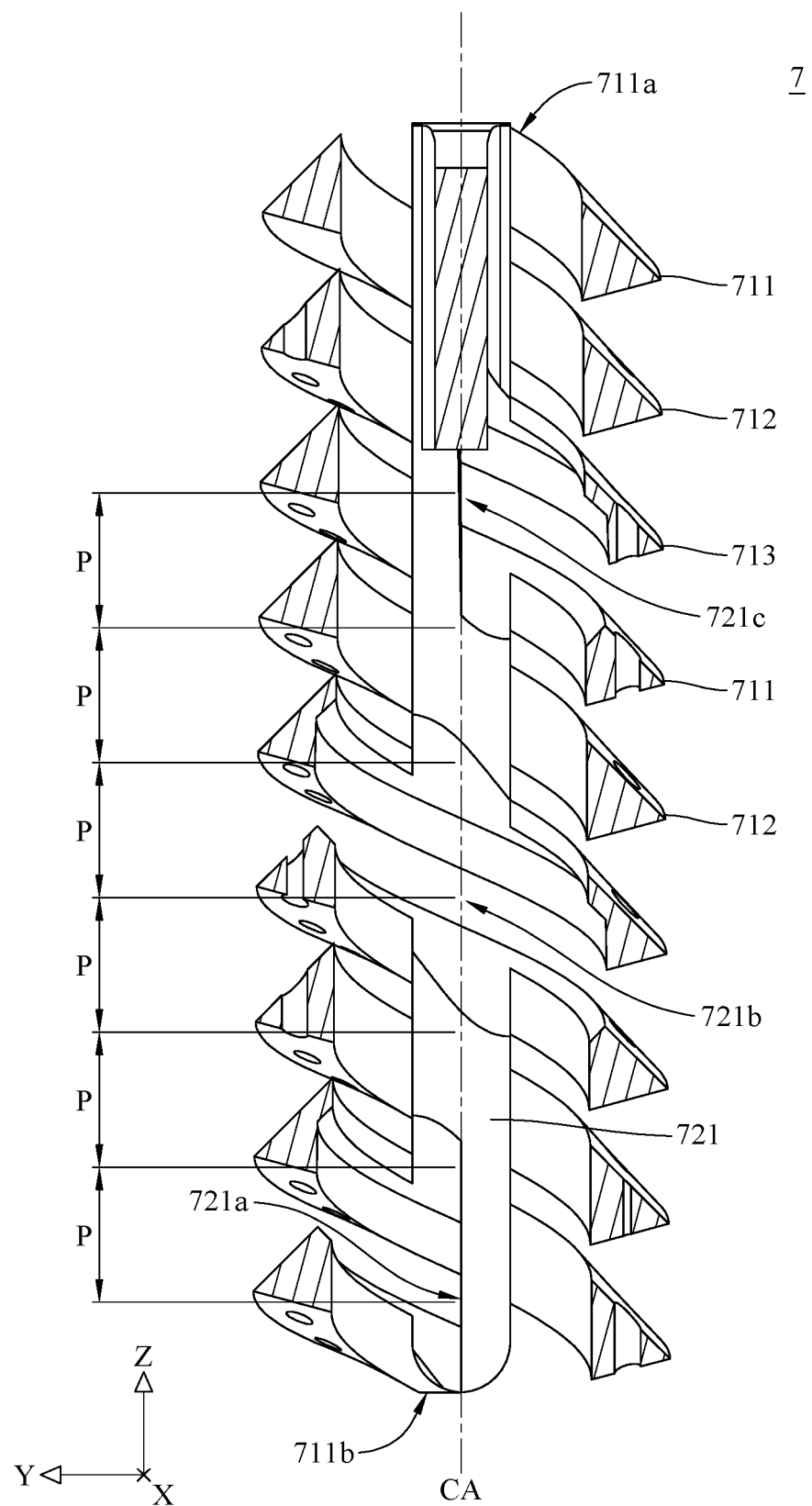
FIG. 19 is a cross-sectional view of the bone implant in FIG. 18.
Figure 20:
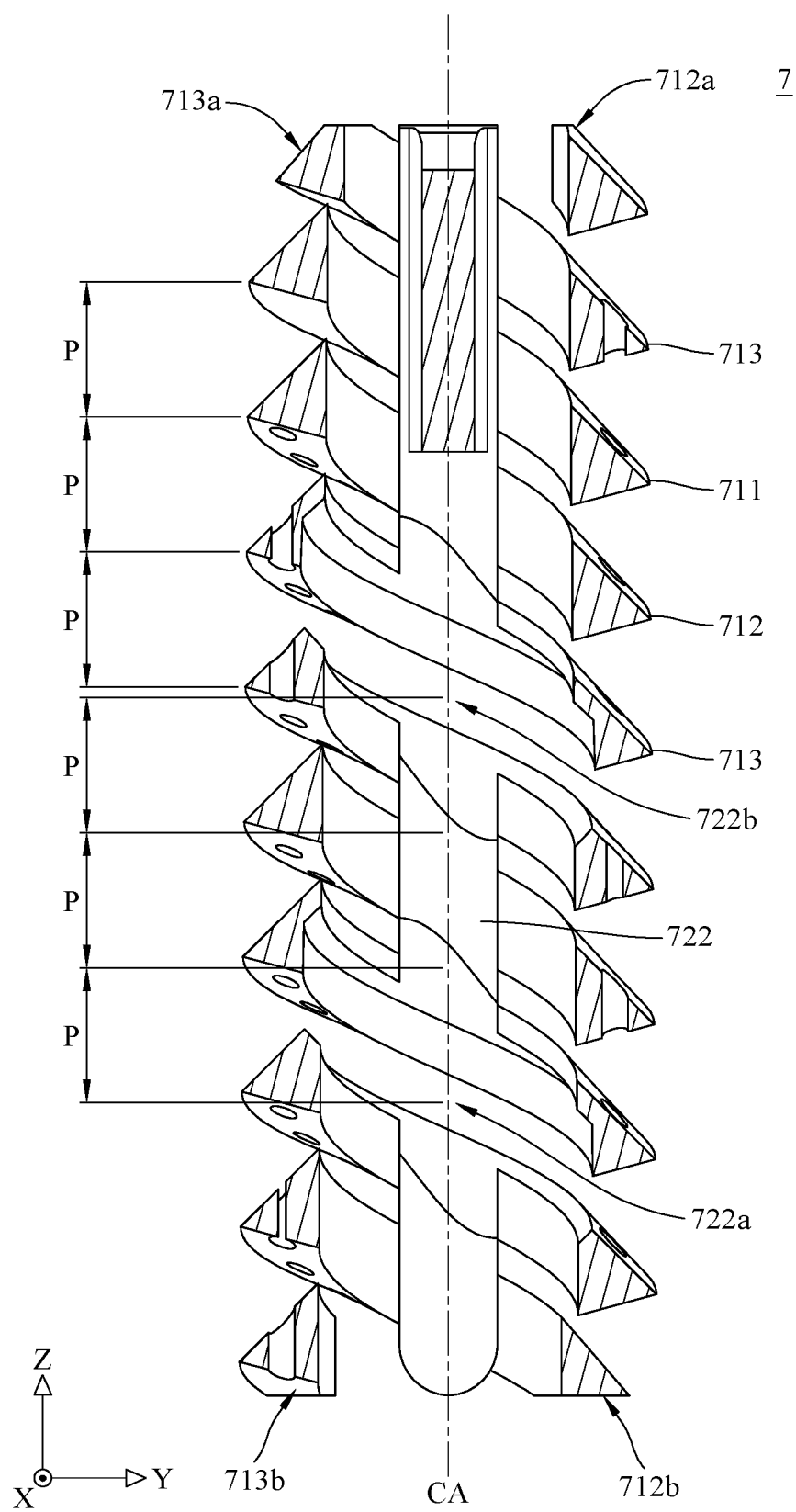
FIG. 20 is another cross-sectional view of the bone implant in FIG. 18.

Please refer to FIG. 18 to FIG. 20. FIG. 18 is a perspective view of a bone implant according to still a further embodiment of the disclosure. FIG. 19 is a cross-sectional view of the bone implant in FIG. 18. FIG. 20 is another cross-sectional view of the bone implant in FIG. 18. This embodiment provides a bone implant 7, and the bone implant 7 is similar to the bone implant 3 in FIG. 8.

It is noted that in this embodiment, the bone implant 7 may have three helix bodies 711, 712 and 713. In this embodiment, the end portion 711a of the helix body 711, the end portion 712a of the helix body 712 and the end portion 713a of the helix body 713 surround the accommodating space S from different positions and extend with a same direction respectively. In detail, the helix bodies 711, 712 and 713 are radially offset with an angle difference of 120 degrees from the central axis CA, and coaxial surround 3 turns about the central axis CA of the accommodating space S respectively.

A distance between two adjacent turns of two helix bodies among the helix bodies 711, 712 and 713 in the direction parallel to the central axis CA is defined as a pitch P In this embodiment, each turn of the helix body 711 corresponds to a distance in the direction parallel to the central axis CA equal to three times of pitch P, each turn of the helix body 712 corresponds to a distance in the direction parallel to the central axis CA equal to three times of pitch P, and each turn of the helix body 713 corresponds to a distance in the direction parallel to the central axis CA equal to three times of pitch P.

In this embodiment, the pillar 721 is disposed in the accommodating space S and is inseparably connected to the helix bodies 711, 712 and 713. The pillar 721 may have a narrowing type of notch 721a, a truncated type of notch 721b and a narrowing type of notch 721c located in order from the end portions 711b, 712b and 713b to the end portions 711a, 712a and 713a. A distance between a center of the notch 721a and a center of the notch 721b may be equal to three times of pitch P, and a distance between the center of the notch 721b and a center of the notch 721c may be equal to three times of pitch P, but the present disclosure is not limited thereto.

In this embodiment, the pillar 722 is disposed in the accommodating space S and is inseparably connected to the helix bodies 711, 712 and 713. The pillar 722 may have two truncated type of notches 722a and 722b located in order from the end portions 711b, 712b and 713b to the end portions 711a, 712a and 713a. A distance between a center of the notch 722a and a center of the notch 722b may be equal to three times of pitch P, but the present disclosure is not limited thereto.

In this embodiment, the notches 721a and 721b of the pillar 721 and the notch 722a of the pillar 722 are located closer to the end portions 711b, 712b and 713b than the end portions 711a, 712a and 713a. The notches 721c and 722b are located closer to the end portions 711a, 712a and 713a than the end portions 711b, 712b and 713b, but the present disclosure is not limited thereto. In other embodiments, the quantities and the arrangement of the notches on the pillars 721 and 722 may be modified according to the required flexibility of the bone implant 7. The flexibility of the bone implant 7 may be increased due to the narrowing type of notches and/or the truncated type of notches on the pillars 721 and/or 722.

The following introduces a plurality of bone implants similar to the bone implant 7 in FIG. 18 with unchanged parameters in the quantities of the pillars, the quantities of the notches, the pitch quantities of the distances between the notches, the quantities of the helix bodies, the outer diameters of the helix bodies, the lengths of the helix bodies, and the thread depths of the helix bodies. Compare with the maximum axial displacements of the bone implants in the central axis CA in different amount of turns. The larger displacement of the bone implant in the central axis CA, the greater flexibility. The results are shown in Table 2.

TABLE 2

| amount of turns | maximum axial displacement (mm) |
|---|---|
| 3 | 0.1147 |
| 3.25 | 0.1215 |
| 3.5 | 0.1211 |
| 3.75 | 0.04917 |

It can be seen that the bone implants with the helix bodies in 3, 3.25 and 3.5 turns have larger maximum axial displacements than the other and thus having greater flexibility.

Figure 21:
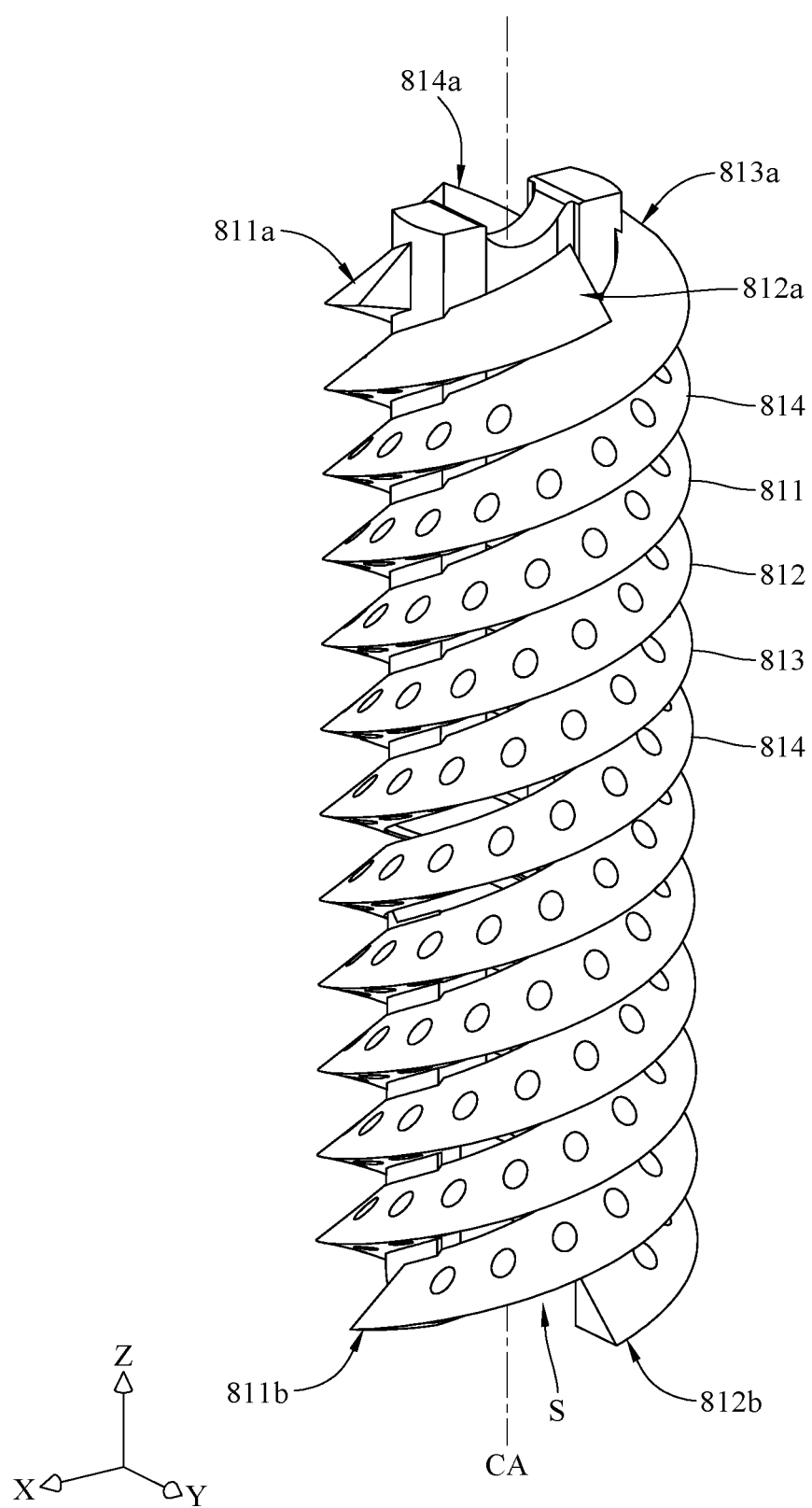
FIG. 21 is a perspective view of a bone implant according to yet a further embodiment of the disclosure.
Figure 22:
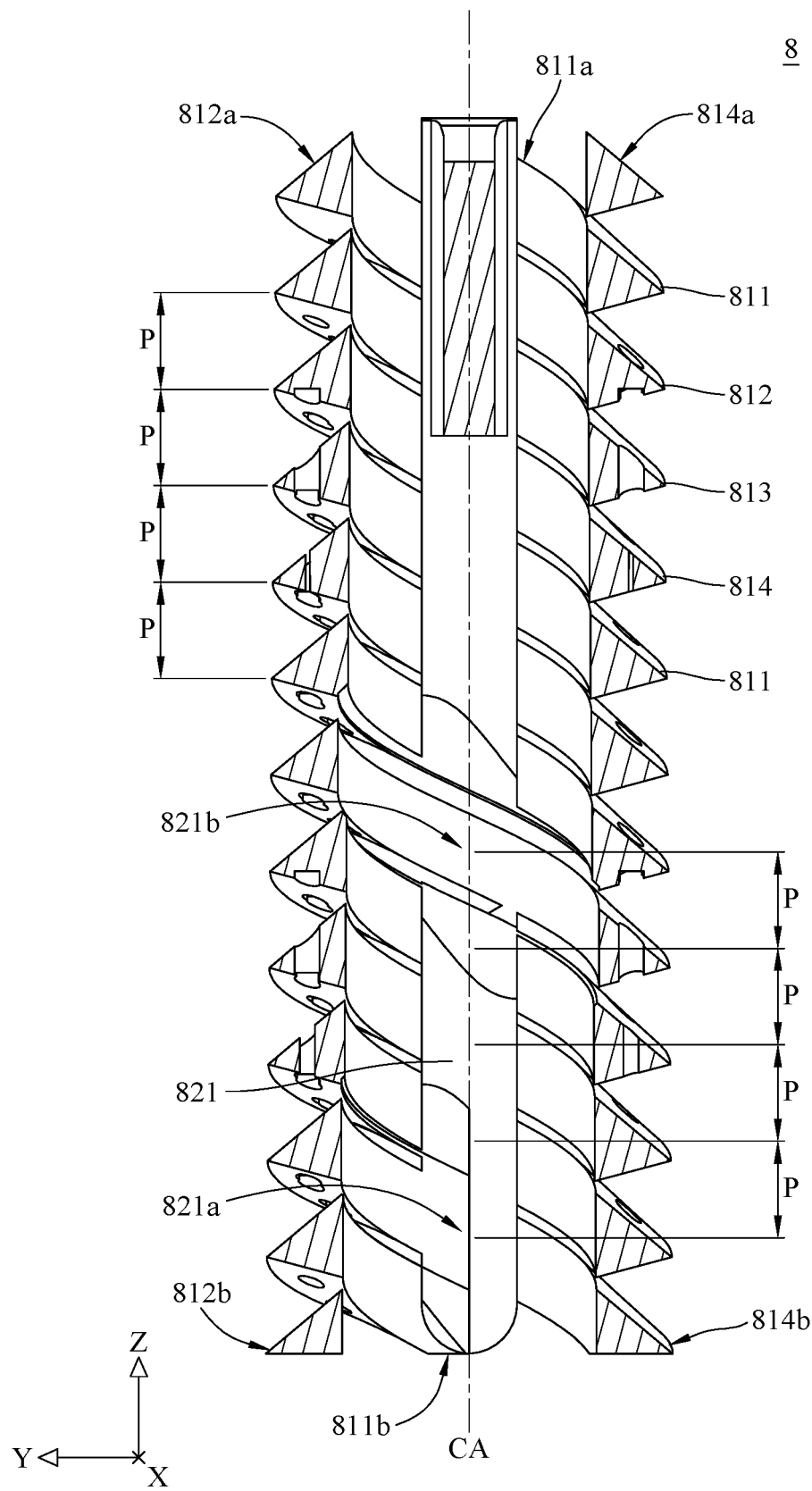
FIG. 22 is a cross-sectional view of the bone implant in FIG. 21.
Figure 23:
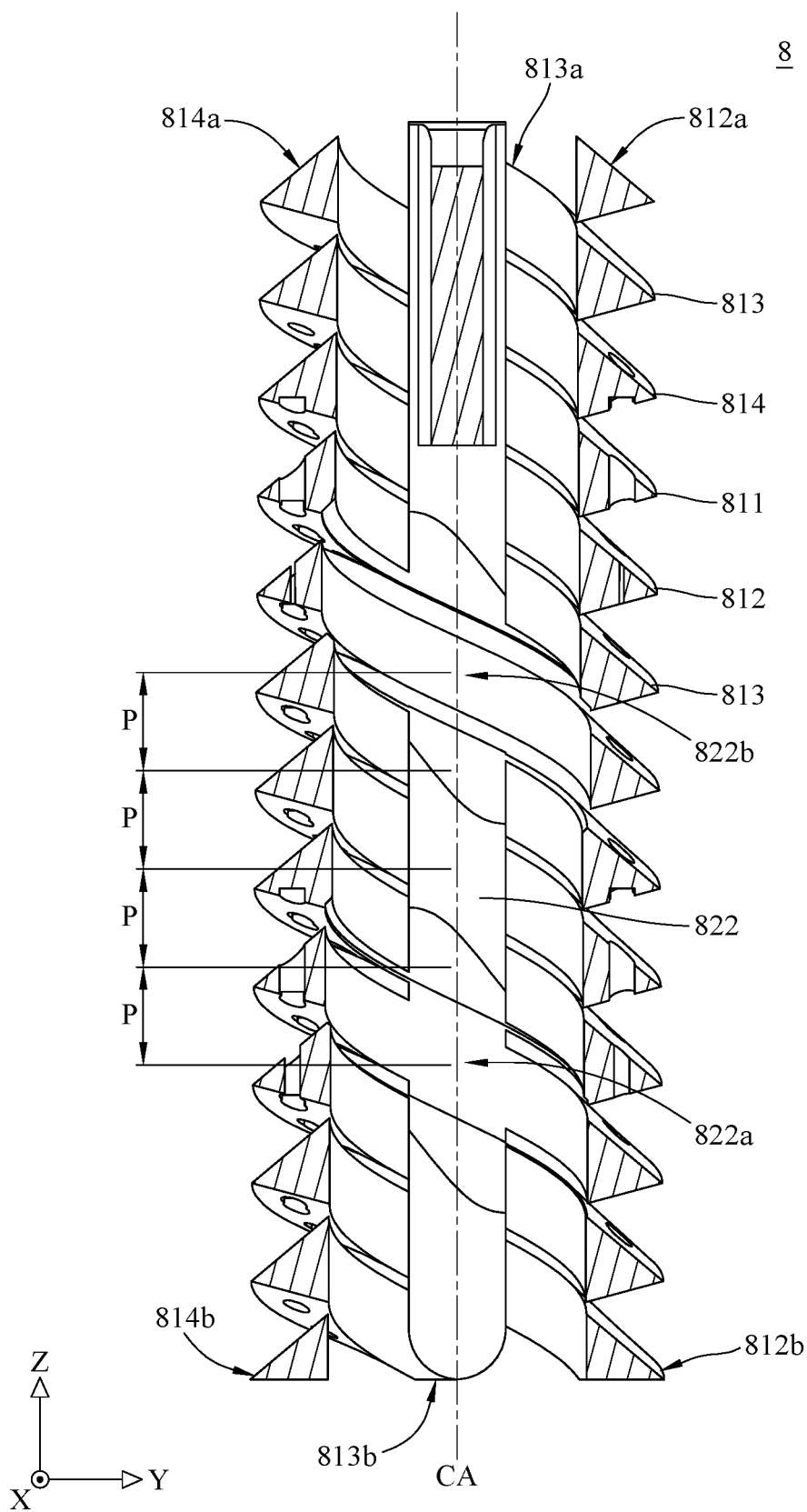
FIG. 23 is another cross-sectional view of the bone implant in FIG. 21.

Please refer to FIG. 21 to FIG. 23. FIG. 21 is a perspective view of a bone implant according to yet a further embodiment of the disclosure. FIG. 22 is a cross-sectional view of the bone implant in FIG. 21. FIG. 23 is another cross-sectional view of the bone implant in FIG. 21. This embodiment provides a bone implant 8, and the bone implant 8 is similar to the bone implant 3 in FIG. 8.

It is noted that, in this embodiment, the bone implant 8 may have four helix bodies 811, 812, 813 and 814. In this embodiment, the end portion 811a of the helix body 811, the end portion 812a of the helix body 812, the end portion 813a of the helix body 813 and the end portion 814a of the helix body 814 surround the accommodating space S from different positions and extend with a same direction respectively. In detail, the helix bodies 811, 812, 813 and 814 are radially offset with an angle difference of 90 degrees from the central axis CA, and coaxial surround 3 turns about the central axis CA of the accommodating space S respectively.

A distance between two adjacent turns of two helix bodies among the helix bodies 811, 812, 813 and 814 in the direction parallel to the central axis CA is defined as a pitch P. In this embodiment, each turn of the helix body 811 corresponds to a distance in the direction parallel to the central axis CA equal to four times of pitch P, each turn of the helix body 812 corresponds to a distance in the direction parallel to the central axis CA equal to four times of pitch P, each turn of the helix body 813 corresponds to a distance in the direction parallel to the central axis CA equal to four times of pitch P and each turn of the helix body 814 corresponds to a distance in the direction parallel to the central axis CA equal to four times of pitch P.

In this embodiment, the pillar 821 is disposed in the accommodating space S and is inseparably connected to the helix bodies 811, 812, 813 and 814. The pillar 821 may have a narrowing type of notch 821a and a truncated type of notch 821b located in order from the end portions 811b, 812b, 813b and 814b to the end portions 811a, 812a, 813a and 814a. A distance between a center of the notch 821a and a center of the notch 821b may be equal to four times of pitch P, but the present disclosure is not limited thereto.

In this embodiment, the pillar 822 is disposed in the accommodating space S and is inseparably connected to the helix bodies 811, 812, 813 and 814. The pillar 822 may have a narrowing type of notch 822a and a truncated type of notch 822b located in order from the end portions 811b, 812b, 813b and 814b to the end portions 811a, 812a, 813a and 814a. A distance between a center of the notch 822a and a center of the notch 822b may be equal to four times of pitch P, but the present disclosure is not limited thereto.

In this embodiment, the notches 821a and 821b of the pillar 821 and the notch 822a of the pillar 822 are located closer to the end portions 811b, 812b, 813b and 814b than the end portions 811a, 812a, 813a and 814a. The notch 822b of the pillar 822 is located closer to the end portions 811a, 812a, 813a and 814a than the end portions 811b, 812b, 813b and 814b, but the present disclosure is not limited thereto. In other embodiments, the quantities and the arrangement of the notches on the pillars 821 and 822 may be modified according to the required flexibility of the bone implant 8. The flexibility of the bone implant 8 may be increased due to the narrowing type of notches and/or the truncated type of notches on the pillars 821 and/or 822.

The following introduces a plurality of bone implants similar to the bone implant 8 in FIG. 21 with unchanged parameters in the quantities of the pillars, the quantities of the notches, the pitch quantities of the distances between the notches, the quantities of the helix bodies, the outer diameters of the helix bodies, the lengths of the helix bodies, and the thread depths of the helix bodies. Compare with the maximum axial displacements of the bone implants in the central axis CA in different amount of turns. The larger displacement of the bone implant in the central axis CA, the greater flexibility. The results are shown in Table 3.

TABLE 3

| amount of turns | maximum axial displacement (mm) |
|---|---|
| 2 | 0.1079 |
| 2.25 | 0.1499 |
| 2.5 | 0.1490 |
| 2.75 | 0.1531 |
| 3 | 0.1686 |

It can be seen that the larger turns of the helix bodies of the bone implants in 2 to 3 turns make the greater maximum axial displacement and thus having greater flexibility.

Figure 24:
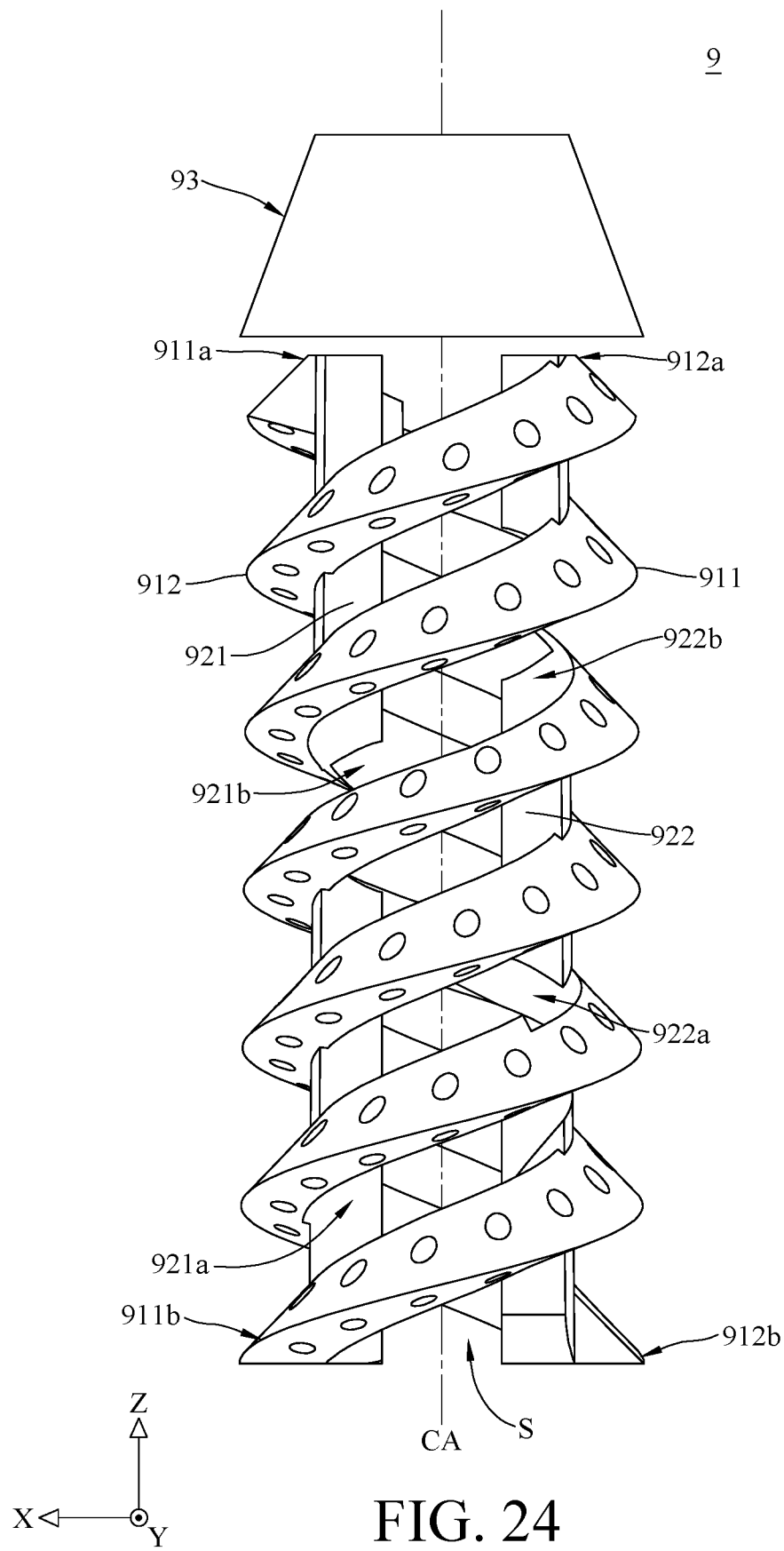
FIG. 24 is a perspective view of a bone implant according to still yet a further embodiment of the disclosure.
Figure 25:
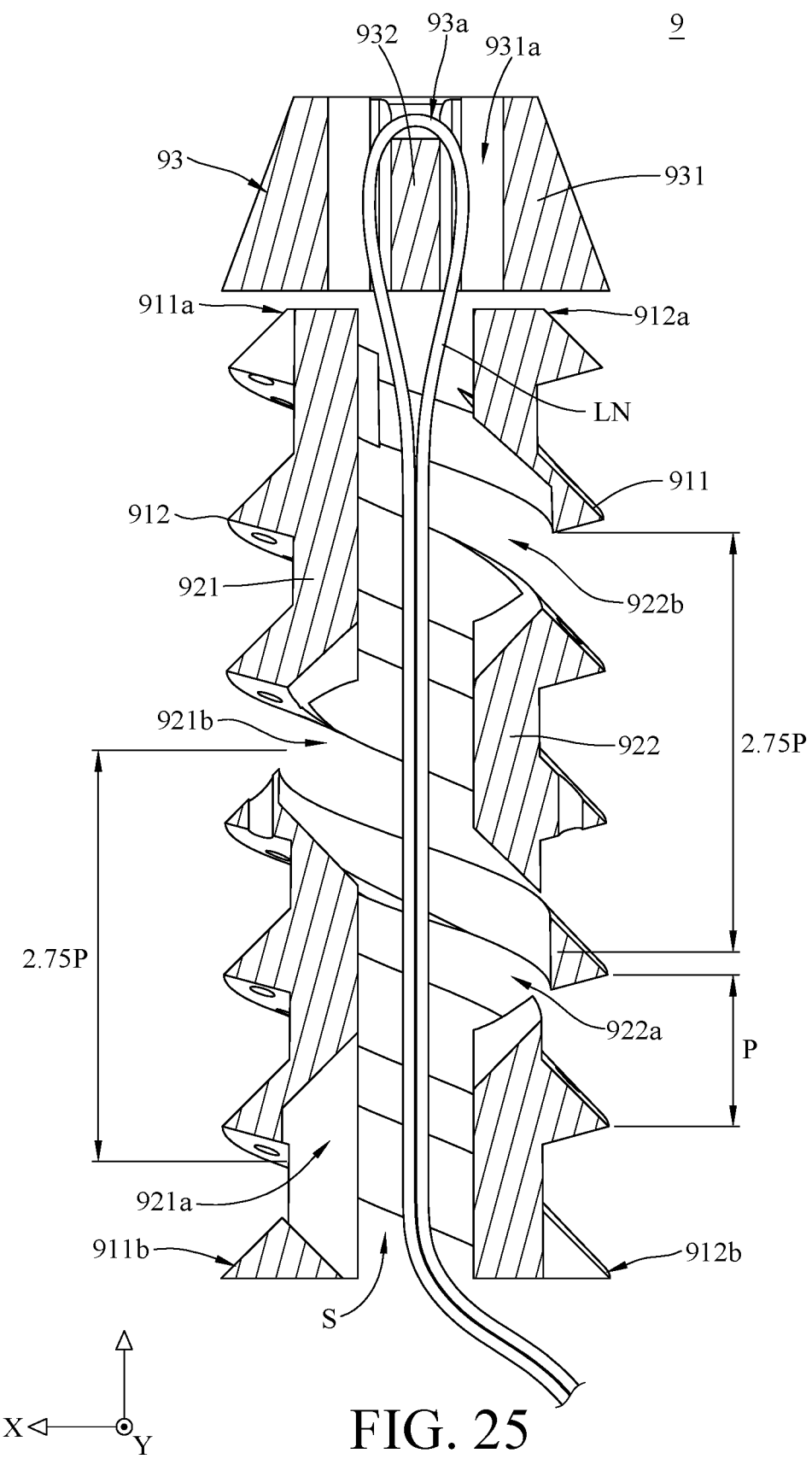
FIG. 25 is a cross-sectional view of the bone implant in FIG. 24.

Please refer to FIG. 24 and FIG. 25. FIG. 24 is a perspective view of a bone implant according to still yet a further embodiment of the disclosure. FIG. 25 is a cross-sectional view of the bone implant in FIG. 24.

This embodiment provides a bone implant 9. The bone implant 9 may include two helix bodies 911 and 912, two pillars 921 and 922 and a holding block 93.

In this embodiment, the helix bodies 911 and 912 are radially offset with an angle difference of 180 degrees from a central axis CA, and coaxial surround 3 turns about the central axis CA of the accommodating space S respectively, but the present disclosure is not limited thereto. In some other embodiments, the quantity of the helix bodies and/or the quantity of the turns may be modified.

In this embodiment, the quantity of the helix bodies 911 and 912 is two, but it is not restricted.

In this embodiment, the pillar 921 is disposed in the accommodating space S and is inseparably connected to the helix bodies 911 and 912. The pillar 921 may have a narrowing type of notch 921a and a truncated type of notch 921b located in order from the end portions 911b and 912b to the end portions 911a and 912a. A distance between a center of the notch 921a and a center of the notch 921b may be equal to 2.75 times of pitch P, but the present disclosure is not limited thereto.

In this embodiment, the pillar 922 is disposed in the accommodating space S and is inseparably connected to the helix bodies 911 and 912. The pillar 922 may have two truncated type of notches 921a and 921b located in order from the end portions 911b and 912b to the end portions 911a and 912a. A distance between a center of the notch 922a and a center of the notch 922b may be equal to 2.75 times of pitch P, but the present disclosure is not limited thereto.

In this embodiment, the notch 921a of the pillar 921 and the notch 922a of the pillar 922 are located closer to the end portions 911b and 912b than the end portions 911a and 912a. The notches 921b and 922b are located closer to the end portions 911a and 912a than the end portions 911b and 912b, but the present disclosure is not limited thereto. In other embodiments, the quantities and the arrangement of the notches on the pillars 921 and 922 may be modified according to the required flexibility of the bone implant 9. The flexibility of the bone implant 9 may be increased due to the narrowing type of notches and/or the truncated type of notches on the pillars 921 and/or 922.

The holding block 93 is detachably disposed on the end portion 911a of the helix body 911 and the end portion 912a of the helix body 912. The holding block 93 includes an outer part 931 and a stopper 932. The outer part 931 may be in a cone shape and has a through hole 931a which is in a cylinder shape. A bottom surface of the outer part 931 faces the helix bodies 911 and 912. The stopper 932 is disposed in the through hole 931a and inseparably connected to the outer part 931. The stopper 932 has a recess 93a formed on a surface of the stopper 932 facing away from the helix bodies 911 and 912.

Before the bone implant 9 is implanted into bone, a suture LN can be disposed through the through hole 931a of the outer part 931 so as to be looped on the stopper 932 and located at the recess 93a of the stopper 932, such that a part of the suture LN is in the through hole 931a and the recess 93a. And then, the other part of the suture LN is disposed into the accommodating space S from the ends portions 911a and 912a to the ends portions 911b and 912b so as to be disposed through the helix bodies 911 and 912.

Then, the holding block 93 may be placed in a manmade hole on the bone, and the end portions 911a and 912a of the helix bodies 911 and 912 are then placed against the holding block 93. And then, the tool for screwing the bone implant 9 is placed into the accommodating space S to clamp the pillars 921 and 922 without interfering with the suture LN, such that the pillars 921 and 922 and the helix bodies 911 and 912 can be rotated about the central axis CA while the pillars 921 and 922 are being rotated by the tool. As a result, the helix bodies 911 and 912 are gradually screwed into the bone and thus pushing the holding block 93 deeper into the bone. Finally, the bone implant 9 is completely implanted into the bone. While implanting the bone implant 9, the holding block 93 does not rotate so that the suture LN does not rotate and will not be tangled.

According to the bone implants as discussed above, the bone implant has the pillar to maintain the overall structural strength and has the notches to improve the flexibility. As such, the bone implants of the disclosure are able to decrease the movement limitation to the injury portion and prevent itself from being detached. In addition, in one of the embodiments of the disclosure, the holding block may be detachable form the helix body, such that the suture will not be rotated with the helix body, thereby preventing the suture from being tangled.

It will be apparent to those skilled in the art that various modifications and variations can be made to the present disclosure. It is intended that the specification and examples be considered as exemplary embodiments only, with a scope of the disclosure being indicated by the following claims and their equivalents.

SYMBOL DESCRIPTION

| | |
|---|---|
| 1, 2, 3, 4, 5, 6, 7, 8, 9 | bone implant |
| 11, 211, 212, 311, 312, 411, 412, 511, 512, 611 | helix body |
| 612, 711, 712, 713, 811, 812, 813, 814, 911, 912 | helix body |
| 11a, 11b, 211a, 211b, 212a, 212b, 411a | end portion |
| 411b, 412a, 412b, 511a, 511b, 512a, 512b | end portion |
| 611a, 611b, 612a, 612b, 711a, 711b, 712a | end portion |
| 712b, 713a, 713b, 811a, 811b, 812a, 812b | end portion |
| 813a, 813b, 814a, 814b, 911a, 911b, 912a, 912b | end portion |
| 12, 221, 222, 421, 422, 521, 522 | pillar |
| 621, 622, 721, 722, 821, 822, 921, 922 | pillar |
| 12a, 12b, 221a, 221b, 222a, 222b, 421a | notch |
| 421b, 421c, 422a, 422b, 422c, 521a, 521b | notch |
| 521c, 522a, 522b, 522c, 621a, 621b, 621c | notch |
| 622a, 622b, 721a, 721b, 721c, 722a, 722b | notch |
| 821a, 821b, 822a, 822b, 921a, 921b, 922a, 922b | notch |
| 13, 23, 93 | holding block |
| 13a, 23a, 93a | recess |
| 31a | hole |
| 641, 642 | wall |
| 931 | outer part |
| 931a | through hole |
| 932 | stopper |
| CA | central axis |
| D | outer diameter |
| H | thread depth |
| L | length |
| LN | suture |
| P | length |
| S | accommodating space |
| W1, W2 | minimum width |

The invention claimed is:

1. A bone implant, comprising:
   at least one helix body surrounding an accommodating space; and
   at least one pillar disposed in the accommodating space and connected to the at least one helix body, wherein the at least one pillar has a plurality of first notches and a plurality of second notches, the plurality of first notches narrow the at least one pillar, the plurality of second notches divide the at least one pillar in parts, and the plurality of first notches and the plurality of second notches are arranged in an alternate arrangement.

2. The bone implant according to claim 1, wherein the at least one pillar is inseparably connected to the at least one helix body.

3. The bone implant according to claim 1, further comprising a holding block, wherein the holding block is inseparably disposed on at least one of the at least one pillar and the at least one helix body.

4. The bone implant according to claim 1, further comprising a holding block, wherein the holding block is detachably disposed on an end portion of the at least one helix body.

5. The bone implant according to claim 1, further comprising a holding block, wherein the holding block is disposed on the at least one helix body, and the holding block has a recess formed on a surface of the at least one holding block facing away from an end portion of the at least one helix body.

6. The bone implant according to claim 1, wherein the quantity of the at least one helix body is plural, the helix bodies are radially offset from a central axis of one of the helix bodies and coaxial surround about the central axis of the accommodating space.

7. The bone implant according to claim 6, the quantity of the helix bodies ranges from 2 to 4.

8. The bone implant according to claim 1, wherein the at least one helix body consists of turns ranging from 2 to 6.

9. The bone implant according to claim 1, wherein the quantity of the at least one pillar is plural, the pillars are respectively located at different sides of a central axis of the at least one helix body.

10. The bone implant according to claim 1, wherein the at least one helix body has a plurality of holes.

11. The bone implant according to claim 1, further comprising at least one wall inseparably connected to the at least one helix body, extending from the at least one helix body in a central axis and surrounding the accommodating space.

12. The bone implant according to claim 11, wherein the at least one wall has a plurality of holes.

13. The bone implant according to claim 1, wherein the at least one helix body has an outer diameter and a length in a central axis of the accommodating space, and the outer diameter and the length have a ratio between 1 and 1/15.

14. The bone implant according to claim 1, wherein the accommodating space has a minimum width in a radial direction passing through a central axis of the accommodating space, and the minimum width is more than 0.9 mm.

15. The bone implant according to claim 1, wherein the at least one helix body has a plurality of pitches, and the at least one pillar has the at least one notch in every one to four pitches.

16. A bone implant, comprising:
   at least one helix body surrounding an accommodating space; and at least one pillar disposed in the accommodating space and connected to the at least one helix body, wherein the at least one pillar has a plurality of notches, wherein at least one of the plurality of notches narrows the at least one pillar, the quantity of the at least one helix body is plural, the helix bodies are radially offset from a central axis of one of the helix bodies and coaxial surround about the central axis of the accommodating space.

* * * * *